United States Patent
Hayashi

[11] Patent Number: 6,070,096
[45] Date of Patent: May 30, 2000

[54] FLUORESCENCE DETECTING APPARATUS

[75] Inventor: Katsumi Hayashi, Kanagawa-ken, Japan

[73] Assignee: Fuji Photo Film Co., Ltd., Kanagawa-ken, Japan

[21] Appl. No.: 09/025,863

[22] Filed: Feb. 19, 1998

Related U.S. Application Data

[62] Division of application No. 08/812,770, Mar. 6, 1997, Pat. No. 5,833,617.

[51] Int. Cl.[7] .............................. G01N 21/64; A61B 6/00
[52] U.S. Cl. ......................................... 600/477; 250/458.1
[58] Field of Search ..................... 600/476, 478, 600/477; 356/317, 318; 250/461.1, 458.1, 363.01, 362

[56] References Cited

U.S. PATENT DOCUMENTS

| | | | |
|---|---|---|---|
| 4,556,057 | 12/1985 | Hiruma et al. | 128/303.1 |
| 4,768,513 | 9/1988 | Suzuki | 128/634 |
| 5,042,494 | 8/1991 | Alfano | 128/665 |
| 5,348,018 | 9/1994 | Alfano et al. | 128/665 |
| 5,421,337 | 6/1995 | Richards-Kortum et al. | 128/665 |
| 5,456,252 | 10/1995 | Vari et al. | 128/633 |
| 5,467,767 | 11/1995 | Alfano et al. | 128/665 |
| 5,507,287 | 4/1996 | Palcic et al. | 128/633 |
| 5,562,100 | 10/1996 | Kittrell et al. | 128/665 |
| 5,590,660 | 1/1997 | MacAulay et al. | 128/664 |
| 5,647,368 | 7/1997 | Zeng et al. | 128/665 |
| 5,769,792 | 6/1998 | Palcic et al. | 600/477 |
| 5,827,190 | 10/1998 | Palcic et al. | 600/476 |
| 5,833,617 | 11/1998 | Hayashi | 600/476 |
| 5,849,595 | 12/1998 | Alfano et al. | 436/164 |
| 5,865,754 | 2/1999 | Sevick-Muraca et al. | 600/476 |

FOREIGN PATENT DOCUMENTS

| | | | |
|---|---|---|---|
| 1-136630 | 5/1989 | Japan | A61B 5/00 |
| 3-58729 | 9/1991 | Japan | A61B 5/00 |
| 7-59783 | 3/1995 | Japan | A61B 10/00 |

OTHER PUBLICATIONS

"Fluorescence Imaging of Early Lung Cancer", Annual International Conference of the IEEE Engineering in Medicine and Biology Society, vol. 12, No. 3, 1990.
"Fluorescence Image Diagnosis of Cancer using Red/Green Ratio" by Tokyo Medical College and Hamamatsu Photonics K.K., 16th Symposium of the Japanese Society of Laser Medical Science, 1995.

Primary Examiner—Marvin M. Lateef
Assistant Examiner—Shawna J Shaw
Attorney, Agent, or Firm—Sughrue, Mion, Zinn, Macpeak & Seas, PLLC

[57] ABSTRACT

A region of interest in a living body is exposed to excitation light, which causes it to produce fluorescence. The fluorescence is separated with respect to desired wavelength ranges and detected. A first detector detects an entire fluorescence component or a fluorescence sum component, which is the sum of a fluorescence component of a comparatively short wavelength region and a fluorescence component of a comparatively long wavelength region. A second detector detects a fluorescence component of a comparatively long wavelength region or a fluorescence difference component, which is the difference between a fluorescence component of a comparatively short wavelength region and a fluorescence component of a comparatively long wavelength region. The output from the first detector and the output from the second detector are divided by each other. The fluorescence intensity depending upon the distance with respect to the region of interest is thus corrected such that no error may occur in making an operation.

6 Claims, 12 Drawing Sheets

F I G. 7
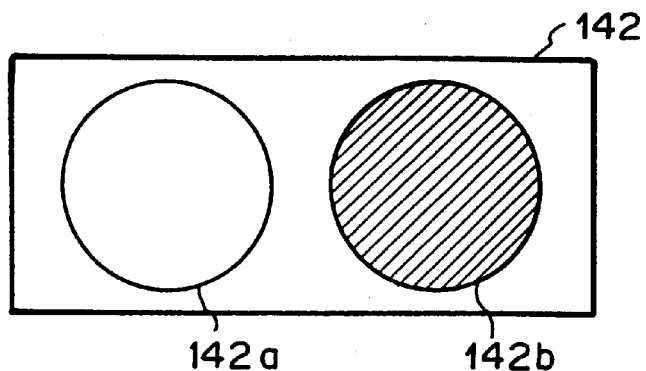
F I G. 8A
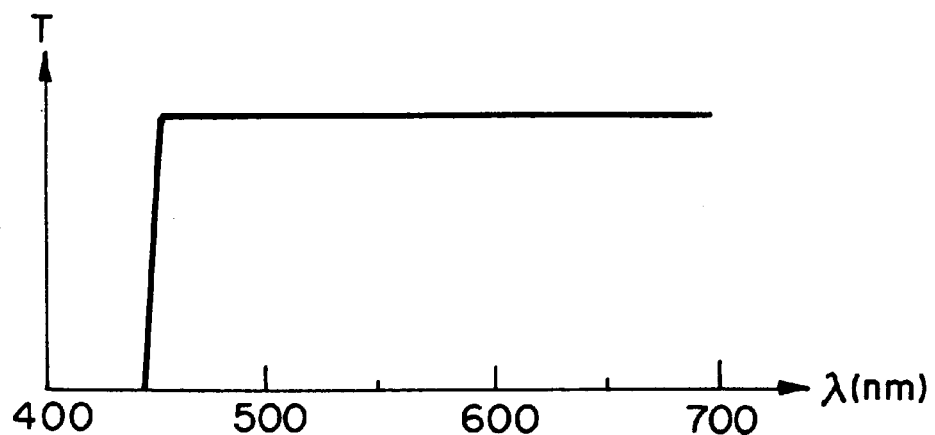
F I G. 8B
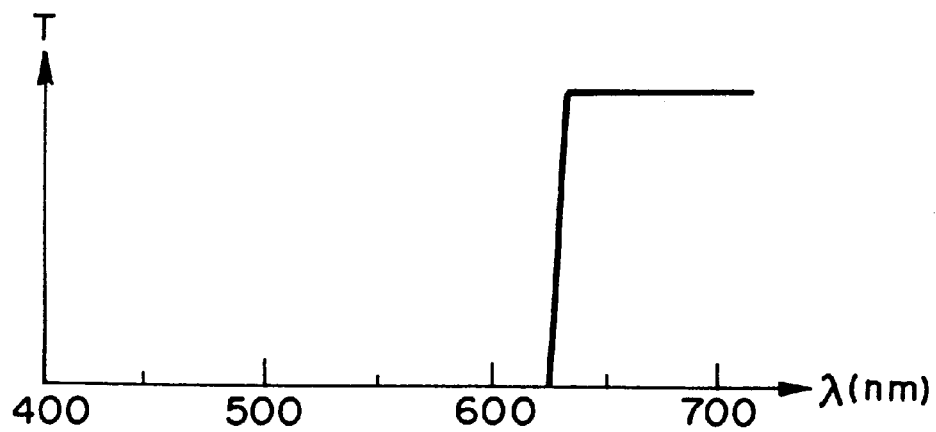

F I G. 9
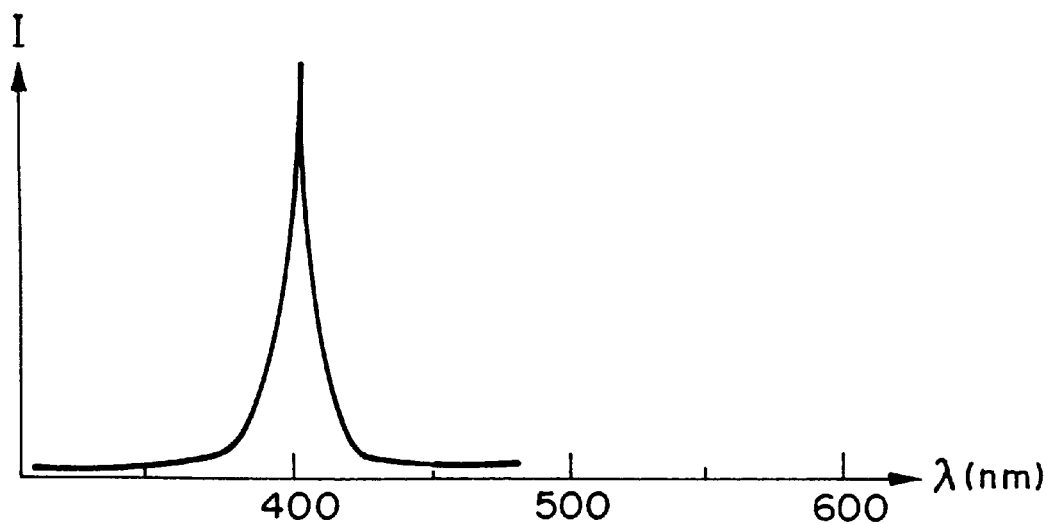
F I G. 10
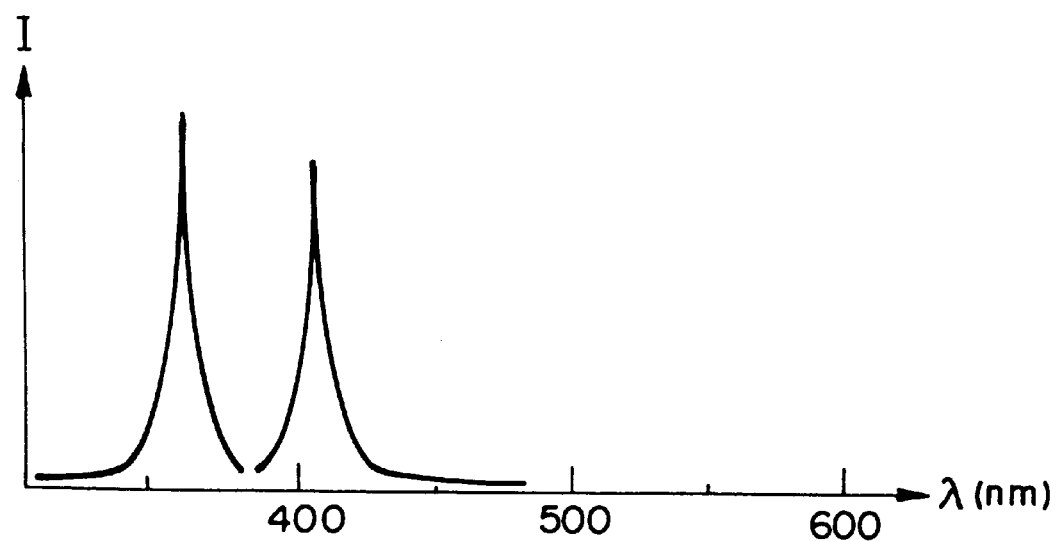

FLUORESCENCE DETECTING APPARATUS

This is a divisional of application Ser. No. 08/812,770 filed Mar. 6, 1997 and now U.S. Pat. No. 5,833,617.

BACKGROUND OF THE INVENTION

1. Field of the Invention

This invention relates to a fluorescence detecting apparatus suitable for use in a fluorescence diagnosing system, wherein a diagnosis of a tumor is carried out by irradiating excitation light to a region of interest in a living body, to which a photosensitive substance, that has a strong affinity for the tumor and is capable of producing fluorescence when it is excited with the excitation light, has been administered, and detecting the intensity of fluorescence, which is produced by the photosensitive substance and an intrinsic dye in the living body when the region of interest in the living body is exposed to the excitation light, or wherein a diagnosis of a tumor is carried out by irradiating excitation light to a region of interest in a living body, to which no photosensitive substance has been administered, and detecting the intensity of intrinsic fluorescence, which is produced by an intrinsic dye in the living body when the region of interest in the living body is exposed to the excitation light.

2. Description of the Prior Art

Extensive research has heretofore been conducted on the so-called photodynamic diagnosis (PDD) technique. With the PDD technique, a photosensitive substance (such as ATX-S10, 5-ALA, NPe6, HAT-D01 or Photofrin-2), which has an affinity for a tumor and is capable of producing fluorescence when it is excited with light, is employed as a fluorescent diagnosis drug. The photosensitive substance is administered to a living body and is absorbed by a tumor part, such as a cancer, of the living body. Excitation light, which has wavelengths falling within the excitation wavelength range for the photosensitive substance, is then irradiated to the region containing the tumor part, and fluorescence is thereby produced from the fluorescent diagnosis drug having been accumulated at the tumor part. By the detection of the fluorescence, the location and infiltration range of the diseased part is displayed as an image, and the displayed image is used in making a diagnosis of the tumor part.

Fluorescence diagnosing systems for carrying out the PDD technique have been disclosed in, for example, U.S. Pat. No. 4,556,057, and Japanese Unexamined Patent Publication Nos. 1(1989)-136630 and 7(1995)-59783. Basically, the disclosed fluorescence diagnosing systems comprise an excitation light irradiating means for irradiating excitation light, which has wavelengths falling within the excitation wavelength range for a photosensitive substance, to a living body, an imaging means for detecting the fluorescence produced by the photosensitive substance and forming a fluorescence image of the living body, and an image displaying means for receiving the output from the imaging means and displaying the fluorescence image. In many cases, the fluorescence diagnosing systems take on the form built in endoscopes, which are inserted into the body cavities, operating microscopes, or the like.

Techniques for making a diagnosis of a tumor part without a photosensitive substance being administered to the living body have also been proposed. With the proposed techniques, excitation light, which has wavelengths falling within the excitation wavelength range for an intrinsic dye in the living body, is irradiated to a region of interest in the living body (i.e., the region which is to be used in making a diagnosis). The intrinsic dye in the living body is thus excited with the excitation light and produces fluorescence. By the detection of the fluorescence, the location and infiltration range of the diseased part is displayed as an image, and the displayed image is used in making a diagnosis of the tumor part.

Further, a different fluorescence diagnosing system has been proposed in, for example, Japanese Patent Application No. 7(1995)-252295. With the proposed fluorescence diagnosing system, instead of the two-dimensional image as described above being formed, the intensity of fluorescence produced from each of different points in a region of a living body is detected. A judgment is then made as to whether each point in the region of the living body belongs or does not belong to a tumor part.

However, the fluorescence diagnosing systems described above have the problems described below. Specifically, since a region in a living body has protrusions and recesses, the distance between the light source of the excitation light irradiating means and the region of interest in the living body is not uniform. Therefore, ordinarily, the irradiance of the excitation light at the living body portion, which is exposed to the excitation light, is non-uniform. In general, the intensity of fluorescence is approximately in proportion to the irradiance of the excitation light, and the irradiance of the excitation light at the portion, which is exposed to the excitation light, is in inverse proportion to the square of the distance between the light source of the excitation light irradiating means and the portion, which is exposed to the excitation light. Accordingly, the problems occur in that a normal part, which is located close to the light source, produces the fluorescence having a higher intensity than the intensity of the fluorescence produced by a diseased part, which is located remote from the light source. The problems also occur in that the intensity of the fluorescence from a diseased part, which is located at a position inclined with respect to the excitation light, becomes markedly low. Thus if the irradiance of the excitation light is non-uniform, the intensity of the fluorescence will vary in accordance with the level of the irradiance of the excitation light, and therefore an error will often be made in diagnosis of a tumor part.

Therefore, fluorescence diagnosing systems, which are designed such that a change in the intensity of fluorescence due to the non-uniformity of the distance with respect to the region of interest in the living body may be compensated for, have been proposed in, for example, U.S. Pat. No. 4,768,513 and Japanese Patent Publication No. 3(1991)-58729. With the fluorescence diagnosing system proposed in Japanese Patent Publication No. 3(1991)-58729, excitation light is irradiated to a portion of a living body, to which a photosensitive substance having a strong affinity for a diseased part has been administered, and the fluorescence produced by the photosensitive substance is detected. Also, the excitation light reflected from the portion of the living body is detected. An image operation is then carried out in accordance with division of the fluorescence component and the reflected excitation light component by each other. By the division, the term due to the distance with respect to the region of interest in the living body is erased. However, in the results of the division of the fluorescence component and the reflected excitation light component by each other, the term concerning the reflectivity of the portion exposed to the excitation light remains unerased. Consequently, the problems remain uneliminated in that a fluorescence image reflecting the distribution of the fluorescent diagnosis drug cannot be obtained.

A different fluorescence imaging technique is proposed in, for example, "Fluorescence Imaging of Early Lung Cancer,"

Annual International Conference of the IEEE Engineering in Medicine and Biology Society, Vol. 12, No. 3, 1990. With the proposed technique, intrinsic fluorescence, which is produced by an intrinsic dye in an region of interest in a living body when the region of interest is exposed to excitation light, is separated into a component of the green wavelength region (hereinbelow referred to as the "green region component G") and a component of the red wavelength region (hereinbelow referred to as the "red region component R"). An image operation is then carried out in accordance with division of the red region component R and the green region component G by each other, and the results of the division are displayed. The proposed technique utilizes the findings in that the spectrum of the intrinsic fluorescence produced by a normal part is different from the spectrum of the intrinsic fluorescence produced by a diseased part. Specifically, when the spectrum of the intrinsic fluorescence, which is produced by the intrinsic dye at a normal part in the living body, and the spectrum of the intrinsic fluorescence, which is produced by the intrinsic dye at a diseased part in the living body, are compared with each other, in particular, the intensity of the green region of the spectrum obtained from the diseased part is markedly lower than the intensity of the green region of the spectrum obtained from the normal part. Therefore, the degree of reduction in the intensity of the green region component G of the intrinsic fluorescence, which is obtained from the diseased part, as compared with the intensity of the green region component G of the intrinsic fluorescence obtained from the normal part, is markedly higher than the degree of reduction in the intensity of the red region component R of the intrinsic fluorescence, which is obtained from the diseased part, as compared with the intensity of the red region component R of the intrinsic fluorescence obtained from the normal part. Therefore, only the intrinsic fluorescence from the diseased part can be specifically extracted by the division of R/G and can be displayed as an image. With the proposed technique, the term of the fluorescence intensity depending upon the distance between the excitation light source and the region of interest in the living body and the distance between the region of interest in the living body and the fluorescence receiving means can be canceled. However, the proposed technique has the problems in that, since the intensity of the intrinsic fluorescence from the diseased part is markedly low, the signal-to-noise ratio cannot be kept high.

Accordingly, a different fluorescence diagnosing technique utilizing an red/green ratio has been proposed in "Fluorescence Image Diagnosis of Cancer Using Red/Green Ratio" by Tokyo Medical College and Hamamatsu Photonics K.K., 16th symposium of The Japanese Society of Laser Medical Science, 1995. With the proposed technique, the intensity of red fluorescence from a diseased part is amplified by using a fluorescent diagnosis drug, which is capable of accumulating at the diseased part and producing red fluorescence, and an operation of R/G is carried out. As a result, a fluorescence image can be obtained such that the intensity of fluorescence from the diseased part may be kept higher than with the aforesaid technique proposed in "Fluorescence Imaging of Early Lung Cancer."

In cases where the operation of R/G is carried out as in the two techniques described above, the term of the fluorescence intensity depending upon the distance between the excitation light source and the region of interest in the living body, which is exposed to the excitation light, and the distance between the region of interest in the living body, which is exposed to the excitation light, and the fluorescence receiving means can be ignored.

However, the intensity of the green intrinsic fluorescence component from the diseased part is markedly low. Therefore, with the two techniques described above, the problems occur in that the division by a value of zero often occurs, and an error readily occurs in making the operation.

SUMMARY OF THE INVENTION

The primary object of the present invention is to provide a fluorescence detecting apparatus, wherein the fluorescence intensity depending upon the distance between an excitation light source and a region of interest in a living body, which is exposed to excitation light, and the distance between the region of interest in the living body, which is exposed to the excitation light, and a fluorescence receiving means is corrected such that no error may occur in making an operation.

Another object of the present invention is to provide a fluorescence detecting apparatus, which enables operation processing with a high signal-to-noise ratio to be carried out.

The specific object of the present invention is to provide a fluorescence detecting apparatus, which enables the formation of a fluorescence image, that has good image quality and is capable of serving as an effective tool in the efficient and accurate diagnosis of an illness.

The present invention provides a first fluorescence detecting apparatus, wherein excitation light is irradiated to a region of interest in a living body, to which a photosensitive substance (i.e., a fluorescent diagnosis drug) has been administered, and fluorescence, which is produced from the region of interest in the living body when the region of interest is exposed to the excitation light, is detected. Specifically, the present invention provides a first fluorescence detecting apparatus, comprising:

i) an excitation light irradiating means for irradiating excitation light to a region of interest in a living body, to which a fluorescent diagnosis drug (i.e., a photosensitive substance), that is capable of producing fluorescence when it is excited with the excitation light, has been administered, the excitation light having wavelengths falling within an excitation wavelength range for the fluorescent diagnosis drug and an intrinsic dye in the living body, which intrinsic dye is capable of producing fluorescence when it is excited with the excitation light, ii) a first fluorescence detecting means for detecting a fluorescence component, which is either one of:

a) an entire fluorescence component having wavelengths falling within a wavelength range, which contains a wavelength range of extrinsic fluorescence, that is produced by the fluorescent diagnosis drug in the region of interest in the living body, and a wavelength range of intrinsic fluorescence, that is produced by the intrinsic dye in the region of interest in the living body, and b) a fluorescence sum component, which is the sum of a fluorescence component having wavelengths falling within a part of the wavelength range of the extrinsic fluorescence, that is produced by the fluorescent diagnosis drug in the region of interest in the living body, and a fluorescence component having wavelengths falling within a part of the wavelength range of the intrinsic fluorescence, that is produced by the intrinsic dye in the living body, iii) a second fluorescence detecting means for detecting a fluorescence component, which is either one of:

a) a fluorescence component having wavelengths falling within a part of the wavelength range of the extrinsic fluorescence, and b) a fluorescence difference component, which is the difference between a fluorescence component, that has wavelengths falling within a part of the wavelength range of the extrinsic fluorescence, and a fluorescence component, that has wavelengths falling within a part of the wavelength range of the intrinsic fluorescence, and iv) a division means for carrying out a division of the fluorescence component, which has been detected by the first fluorescence detecting means, and the fluorescence component, which has been detected by the second fluorescence detecting means, by each other.

In the first fluorescence detecting apparatus in accordance with the present invention, such that the signal-to-noise ratio of the fluorescence component, which is detected by each fluorescence detecting means, may be enhanced, light having wavelengths falling within a wavelength range in the vicinity of an excitation peak wavelength for the fluorescent diagnosis drug should preferably be employed as the excitation light. Alternatively, light having wavelengths falling within a wavelength range in the vicinity of the excitation peak wavelength for the fluorescent diagnosis drug and light having wavelengths falling within a wavelength range in the vicinity of an excitation peak wavelength for the intrinsic dye in the living body should preferably be employed as the excitation light.

The term "excitation peak wavelength for a fluorescent diagnosis drug" as used herein means the wavelength of the excitation light, which causes the fluorescent diagnosis drug to produce the extrinsic fluorescence having the highest possible intensity. Also, the term "excitation peak wavelength for an intrinsic dye in a living body" as used herein means the wavelength of the excitation light, which causes the intrinsic dye in the living body to produce the intrinsic fluorescence having the highest possible intensity.

The present invention also provides a second fluorescence detecting apparatus, wherein excitation light is irradiated to a region of interest in a living body, to which no photosensitive substance (fluorescent diagnosis drug) has been administered, and intrinsic fluorescence, which is produced by an intrinsic dye in the region of interest in the living body when the intrinsic dye is excited with the excitation light, is detected. Specifically, the present invention also provides a second fluorescence detecting apparatus, comprising:

i) an excitation light irradiating means for irradiating excitation light to a region of interest in a living body, the excitation light having wavelengths falling within an excitation wavelength range for an intrinsic dye in the living body, which intrinsic dye is capable of producing fluorescence when it is excited with the excitation light, ii) a first fluorescence detecting means for detecting a fluorescence component, which is either one of:

a) an entire intrinsic fluorescence component having wavelengths falling within a visible wavelength range, which contains a comparatively short wavelength range and a comparatively long wavelength range among the wavelength range of intrinsic fluorescence, that is produced by the intrinsic dye in the region of interest in the living body, and b) a fluorescence sum component, which is the sum of a fluorescence component having wavelengths falling within a part of the comparatively short wavelength range among the wavelength range of the intrinsic fluorescence, that is produced by the intrinsic dye in the region of interest in the living body, and a fluorescence component having wavelengths falling within a part of the comparatively long wavelength range among the wavelength range of the intrinsic fluorescence, iii) a second fluorescence detecting means for detecting a fluorescence component, which is either one of:

a) a fluorescence component having wavelengths falling within a part of the comparatively long wavelength range among the wavelength range of the intrinsic fluorescence, and b) a fluorescence difference component, which is the difference between a fluorescence component, that has wavelengths falling within a part of the comparatively short wavelength range among the wavelength range of the intrinsic fluorescence, and a fluorescence component, that has wavelengths falling within a part of the comparatively long wavelength range among the wavelength range of the intrinsic fluorescence, and iv) a division means for carrying out a division of the fluorescence component, which has been detected by the first fluorescence detecting means, and the fluorescence component, which has been detected by the second fluorescence detecting means, by each other.

In the second fluorescence detecting apparatus in accordance with the present invention, such that the signal-to-noise ratio of the fluorescence component, which is detected by each fluorescence detecting means, may be enhanced, light having wavelengths falling within a wavelength range in the vicinity of an excitation peak wavelength for the intrinsic dye in the living body should preferably be employed as the excitation light.

In the first and second fluorescence detecting apparatuses in accordance with the present invention, each fluorescence detecting means may detect the fluorescence produced from each of different points in the region of interest. Alternatively, each fluorescence detecting means may carry out two-dimensional detection of the fluorescence (the extrinsic fluorescence or the intrinsic fluorescence) produced from the region of interest and may thereby obtain a fluorescence image of the region of interest.

With the first and second fluorescence detecting apparatuses in accordance with the present invention, wherein the entire fluorescence component, which has the wavelengths falling within the predetermined wavelength range, or the fluorescence sum component, which is the sum of the fluorescence components having wavelengths falling within desired wavelength ranges, is employed as the denominator in the division, the value of the denominator in the division can be kept sufficiently large. Therefore, the problems can be prevented from occurring in that an operation error occurs due to division by a value of zero in the image operation. Also, the adverse effects from fluctuation in the intensity of fluorescence due to the distance between the excitation light irradiating means and the region of interest in the living body, which is exposed to the excitation light, and the distance between the region of interest in the living body and a fluorescence receiving means can be eliminated reliably.

Further, in cases where light having wavelengths falling within a wavelength range in the vicinity of the excitation peak wavelength for the fluorescent diagnosis drug and/or light having wavelengths falling within a wavelength range in the vicinity of the excitation peak wavelength for the intrinsic dye in the living body is employed as the excitation light, the values of the denominator and the numerator in the division can be kept sufficiently large. Therefore, operation processing with a high signal-to-noise ratio can be carried out.

The first and second fluorescence detecting apparatuses in accordance with the present invention may be applied to a fluorescence diagnosing system, wherein a fluorescence image is formed by using an imaging means, such as an image sensor, as the fluorescence detecting means. In such cases, a fluorescence image can be obtained, in which the adverse effects from fluctuation in the intensity of fluorescence due to the aforesaid distance have been eliminated. Also, a fluorescence image having good image quality with a high signal-to-noise ratio can be obtained. Therefore, a fluorescence image can be obtained, which has good image quality and is capable of serving as an effective tool in the efficient and accurate diagnosis of an illness.

BRIEF DESCRIPTION OF THE DRAWINGS

FIG. 7 is a schematic view showing a change-over optical filter, which is employed in the first embodiment, FIGS. 8A and 8B are graphs showing light transmission characteristics of the change-over optical filter shown in FIG. 7, FIG. 9 is a graph showing an example of an excitation light spectrum of an excitation light source in the first embodiment, FIG. 10 is a graph showing a different example of an excitation light spectrum of the excitation light source in the first embodiment.

DESCRIPTION OF THE PREFERRED EMBODIMENTS

The present invention will hereinbelow be described in further detail with reference to the accompanying drawings.

Figure 1:
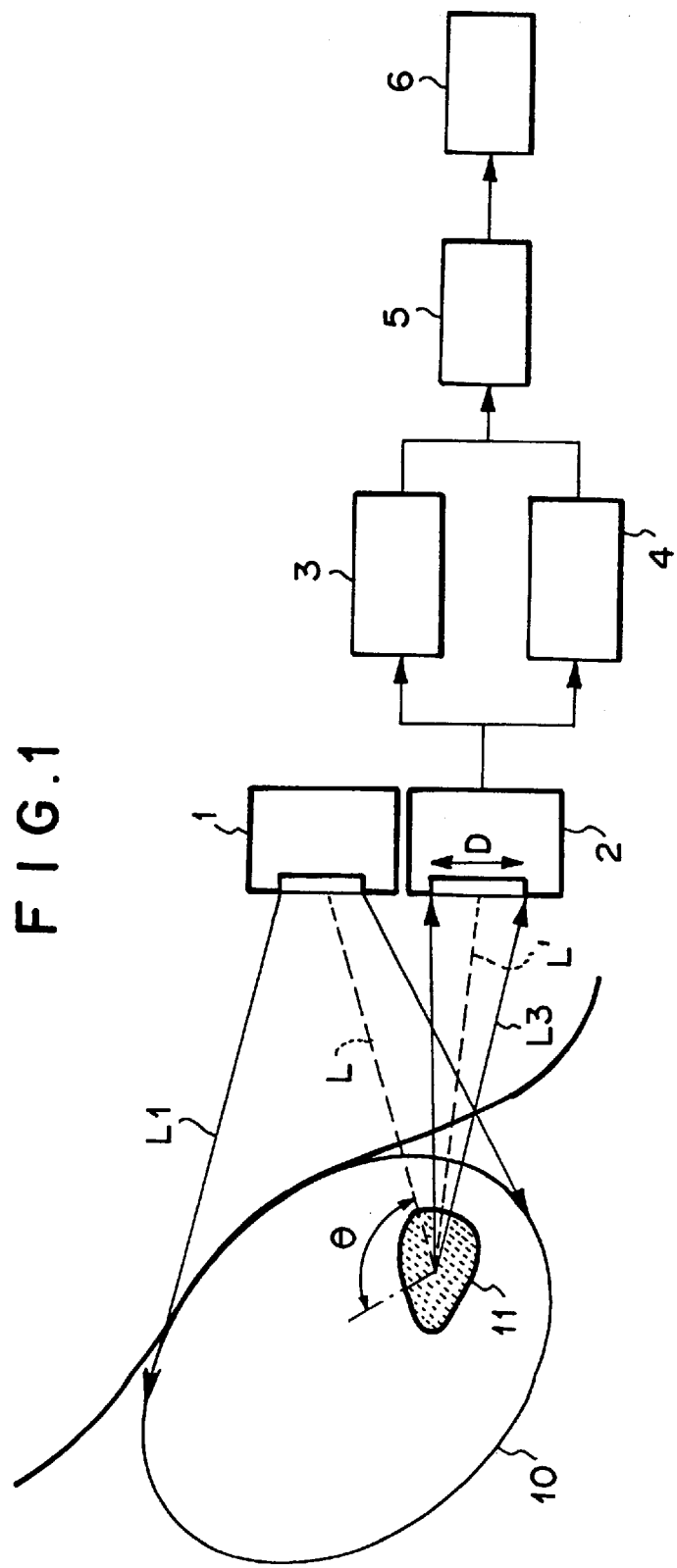
FIG. 1 is an explanatory view showing a fundamental constitution of the fluorescence detecting apparatus in accordance with the present invention.

FIG. 1 shows a fundamental constitution of the fluorescence detecting apparatus in accordance with the present invention. As a fundamental constitution, the fluorescence detecting apparatus comprises an excitation light irradiating means 1 for irradiating excitation light L1 to a region of interest 10 in a living body, and a fluorescence receiving optical system 2 for receiving fluorescence L3, which is produced from the region of interest 10 in the living body. The fluorescence detecting apparatus also comprises a fluorescence detecting means 3 for separating the fluorescence L3 into fluorescence components, which have wavelengths falling within desired wavelength ranges, and detecting a fluorescence component, which has wavelengths falling within a desired wavelength range, or a fluorescence difference component, which is the difference between fluorescence components having wavelengths falling within desired wavelength ranges. The fluorescence detecting apparatus further comprises a fluorescence detecting means 4 for detecting an entire fluorescence component, which has wavelengths falling within a predetermined wavelength range among the wavelength range of the fluorescence L3, or a fluorescence sum component, which is the sum of fluorescence components having wavelengths falling within desired wavelength ranges. The fluorescence detecting apparatus still further comprises a division means 5 for carrying out a dividing operation in accordance with the outputs obtained from the fluorescence detecting means 3 and the fluorescence detecting means 4. By way of example, the output obtained from the division means 5 is fed as image information into a display means 6 for displaying a visible image. Each of the fluorescence detecting means 3 and the fluorescence detecting means 4 may be constituted as a fluorescence detecting means containing the fluorescence receiving optical system 2. In FIG. 1, as an aid in facilitating the explanation, the fluorescence receiving optical system 2 is illustrated as being separated from the fluorescence detecting means 3 and the fluorescence detecting means 4.

How the intensity of fluorescence, which depends upon the distance between an excitation light source of the excitation light irradiating means 1 and the region of interest 10 in the living body, that is exposed to the excitation light, and the distance between the region of interest 10 in the living body and the fluorescence receiving optical system 2, is corrected in the fluorescence detecting apparatus having the fundamental constitution described above will be described hereinbelow.

In a constitution of the fluorescence detecting apparatus, the excitation light is irradiated to the region of interest in the living body, to which the photosensitive substance (i.e., the fluorescent diagnosis drug) has been administered. The extrinsic fluorescence, which is produced by the fluorescent diagnosis drug when the region of interest in the living body is exposed to the excitation light, and the intrinsic fluorescence, which is produced by an intrinsic dye in the region of interest in the living body when the region of interest is exposed to the excitation light, are detected. (Such cases will hereinbelow be referred to as "cases where the fluorescence with the administration of the drug is detected.") Also, in this constitution, an extrinsic fluorescence component Ex and a fluorescence sum component (Ex+In), which is the sum of the extrinsic fluorescence component Ex and an intrinsic fluorescence component In, are divided by each other. The constitution will hereinbelow be described in detail.

The excitation light having a wavelength $\lambda_{ex}$ is produced by the excitation light irradiating means 1 and irradiated to the region of interest 10 in the living body, to which the fluorescent diagnosis drug has been administered and which contains a diseased part 11. When the region of interest 10 in the living body is exposed to the excitation light, the region of interest 10 is excited and produces the fluorescence L3. The fluorescence L3 is received by the fluorescence receiving optical system 2. The fluorescence L3 is separated with respect to wavelength ranges by a dichroic mirror, an optical filter, or the like. The extrinsic fluorescence component, which is produced by the fluorescent diagnosis drug in the region of interest 10 in the living body, and the fluorescence sum component, which is the sum of the extrinsic fluorescence component and the intrinsic fluorescence component, that is produced by the intrinsic dye in the region of interest 10 in the living body, are thereby separated from each other. The fluorescence detecting means 3 detects the extrinsic fluorescence component, and the fluorescence detecting means 4 detects the fluorescence sum component. The photo detecting device employed in each of the fluorescence detecting means 3 and the fluorescence detecting means 4 may be constituted of a photo detecting device, such as a photodiode, which detects the fluorescence L3 for each of different points in the region of interest 10 in the living body. Alternatively, the photo detecting device may be constituted of a charge coupled device image sensor, or the like, which detects the fluorescence L3 in two dimensional directions and forms a fluorescence image. This also applies to the other constitutions, which will be described later.

The wavelength range of the extrinsic fluorescence component, which is detected by the fluorescence detecting means 3, and the wavelength range of the extrinsic fluorescence component, which is contained in the fluorescence sum component detected by the fluorescence detecting means 4, need not necessarily be identical with each other. Also, the means for detecting the extrinsic fluorescence component and the means for detecting the fluorescence sum component are not limited to those employed in this constitution. As an alternative, fluorescence components having wavelengths falling within predetermined wavelength ranges may be separated from each other and detected, and a fluorescence component having wavelengths falling within a wavelength range to be used ultimately may be calculated by carrying out an operation, such as addition or subtraction, on the results of the detection. For example, the fluorescence L3 may be separated with respect to wavelength ranges, and the extrinsic fluorescence component and the intrinsic fluorescence component may thereby be separated from each other. Thereafter, the extrinsic fluorescence component may be detected by the fluorescence detecting means 3, and the intrinsic fluorescence component may be detected by the fluorescence detecting means 4. The outputs obtained from the fluorescence detecting means 3 and the fluorescence detecting means 4 may then be added to each other, and the fluorescence sum component may thereby be obtained. As another alternative, the fluorescence L3 may be separated with respect to wavelength ranges, and the intrinsic fluorescence component and the fluorescence sum component, which is the sum of the extrinsic fluorescence component and the intrinsic fluorescence component, may thereby be separated from each other. Also, the intrinsic fluorescence component may be detected by the fluorescence detecting means 3, and the fluorescence sum component may be detected by the fluorescence detecting means 4. Thereafter, the intrinsic fluorescence component may be subtracted from the fluorescence sum component, and the extrinsic fluorescence component may thereby be obtained.

Figure 2:
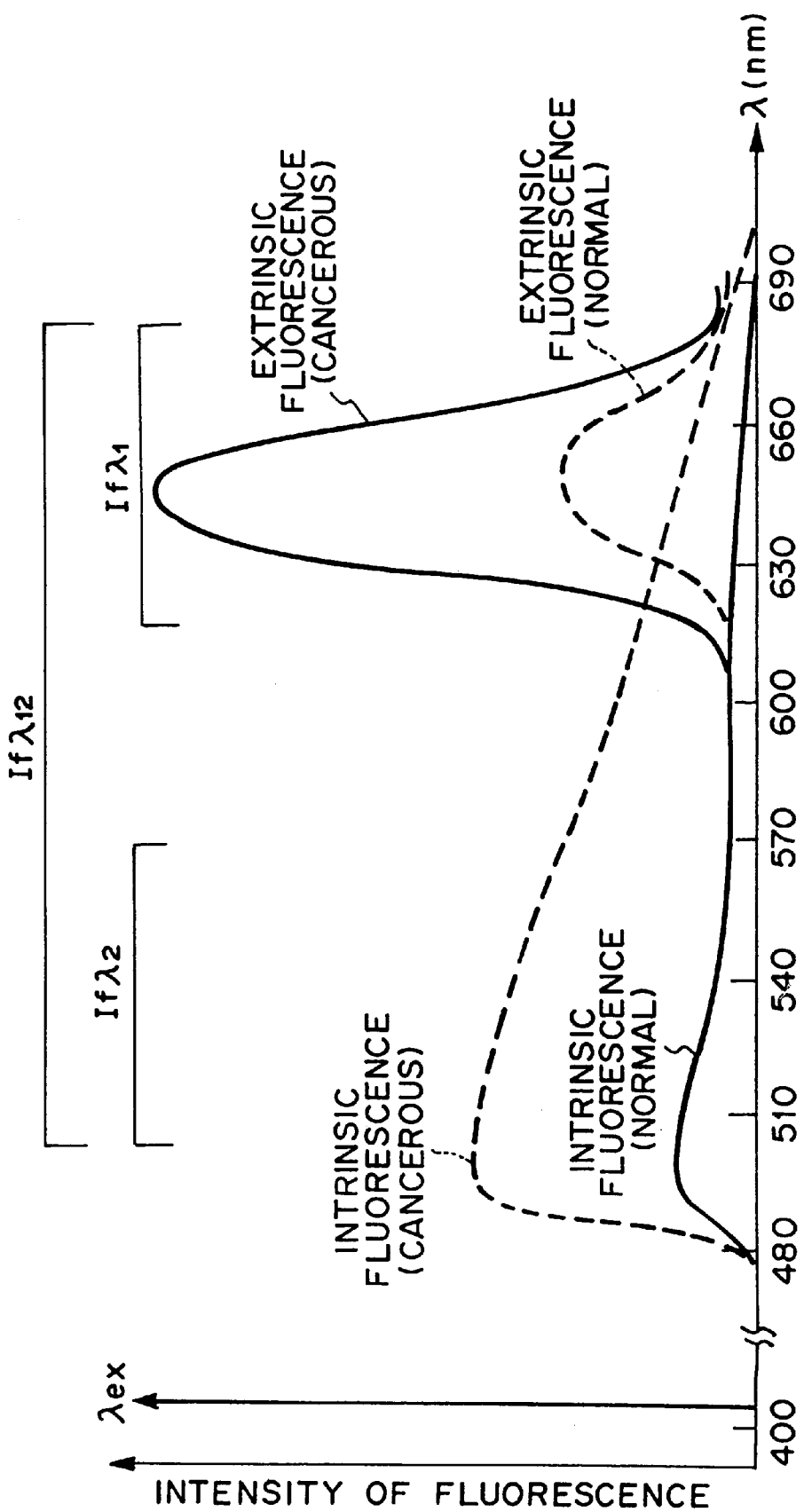
FIG. 2 is a graph showing the relationship among a wavelength $\lambda_{ex}$ of excitation light, an intrinsic fluorescence component If$\lambda_2$, and an extrinsic fluorescence component If$\lambda_1$.

How the fluorescence detecting apparatus having the constitution described above operates will be described hereinbelow. When the excitation light L1 is irradiated to the region of interest 10 in the living body, the region of interest 10 in the living body is excited by the excitation light L1 and produces the fluorescence L3 having a spectrum illustrated in FIG. 2. The fluorescence L3 comprises an intrinsic fluorescence component If$\lambda_2$, which is produced by the intrinsic dye, such as FAD or NADH, in the living body, and an extrinsic fluorescence component If$\lambda_1$, which is produced by the fluorescent diagnosis drug having been accumulated at a diseased part. Ordinarily, the intrinsic fluorescence component If$\lambda_2$ has the maximum peak in the vicinity of a wavelength of 500 nm and attenuates markedly in the region longer than a wavelength of 600 nm. The extrinsic fluorescence component If$\lambda_1$ has the maximum peak at a wavelength longer than 600 nm.

The wavelength components detected by the fluorescence detecting means 3 and the fluorescence detecting means 4 may be represented as described below.

The extrinsic fluorescence component If$\lambda_1$ may be represented by the formula shown below.

$$If\lambda_1 = k\lambda_1 \cdot I\lambda_{ex} \cdot \eta F\lambda_1 \cdot N \cdot \eta D$$

The apparent intrinsic fluorescence component If$\lambda_2$ may be represented by the formula shown below.

$$If\lambda_2 = k\lambda_2 \cdot I\lambda_{ex} \cdot \eta F\lambda_2 \cdot n \cdot \eta D$$

The fluorescence sum component If$\lambda_+$ may be represented by the formula shown below.

$$If\lambda_+ = If\lambda_1 + If\lambda_2$$

Unless otherwise specified, the symbols used herein for the cases where the fluorescence with the administration of the drug is detected have the meanings described below. This also applies to the below-described cases where the fluorescence with the administration of the drug is detected.

$\lambda_{ex}$: The wavelength of the excitation light.

I$\lambda_{ex}$: The intensity of the excitation light at the region of interest in the living body, which intensity depends upon the distance L between the excitation light source and the region of interest in the living body, the power P of the excitation light source, and the angle θ made between the excitation light beam and the region of interest in the living body. $I\lambda_{ex}=I\lambda_{ex}(L, P, \theta)$ n: The concentration of the apparent intrinsic fluorescent molecule. (It is considered that a plurality of kinds of intrinsic fluorescent molecules are present in the living body. They can virtually be processed such that only a single kind of molecule may be present, and therefore the term "apparent" is used herein.)

N: The concentration of the extrinsic fluorescent molecule.

$k\lambda_1$: The fixed number, which depends upon the wavelength $\lambda_{ex}$ of the excitation light and the extrinsic fluorescent molecule.

$k\lambda_2$: The fixed number, which depends upon the wavelength $\lambda_{ex}$ of the excitation light and the apparent intrinsic fluorescent molecule.

$k\lambda_{12}$: The fixed number, which depends upon the wavelength $\lambda_{ex}$ of the excitation light and the apparent fluorescent molecule, that contributes to the fluorescence having wavelengths falling within the entire wavelength range.

$\eta F\lambda_1$: The fluorescence quantum yield of the extrinsic fluorescent molecule with respect to the wavelength $\lambda_{ex}$ of the excitation light.

$\eta F\lambda_2$: The fluorescence quantum yield of the apparent intrinsic fluorescent molecule with respect to the wavelength $\lambda_{ex}$ of the excitation light.

$\eta F\lambda_{12}$: The fluorescence quantum yield of the apparent fluorescent molecule, which contributes to the fluorescence having wavelengths falling within the entire wavelength range, with respect to the wavelength $\lambda_{ex}$ of the excitation light.

$\eta D$: The fluorescence detection efficiency, which depends upon the distance L' between the fluorescence producing site and the fluorescence receiving optical system, the size D of the aperture of the fluorescence receiving optical system, and the efficiency $\xi$ of the photo detecting device. $\eta D=\eta D$ (L', $\xi$, D). (In the strict sense, the detection efficiency with respect to the intrinsic fluorescence and the detection efficiency with respect to the extrinsic fluorescence are different from each other. However, they can herein be processed as being approximately equal to each other.)

Thereafter, the division means 5 carries out the division of the extrinsic fluorescence component $If\lambda_1$ and the fluorescence sum component $If\lambda_+$ by each other. The division may be represented by the formula shown below.

$$If\lambda_1/If\lambda_+ = (k\lambda_1 \cdot \eta F\lambda_1 \cdot N)/(k\lambda_1 \cdot \eta F\lambda_1 \cdot N + k\lambda_2 \cdot \eta F\lambda_2 \cdot n)$$

If $(k\lambda_1 \cdot \eta F\lambda_1)/(k\lambda_2 \cdot \eta F\lambda_2)=C$ and $N/n=X$, the formula shown below will obtain.

$$If\lambda_1/If\lambda_+ = (C \cdot X)/(C \cdot X+1)$$

Figure 3:
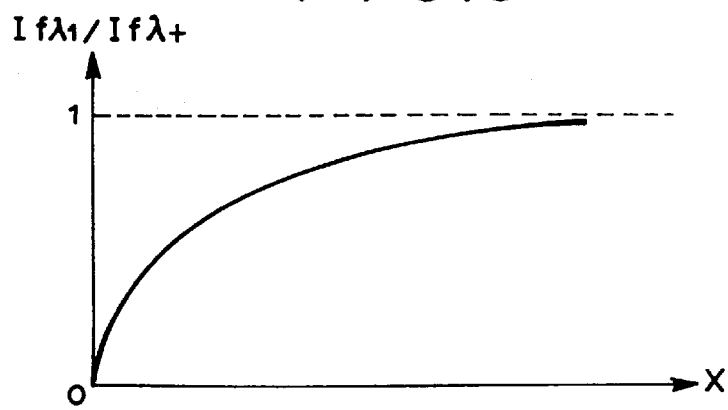
FIG. 3 is a graph showing the relationship between a quotient If$\lambda_1$/If$\lambda_+$, which is obtained by dividing an extrinsic fluorescence component If$\lambda_1$ by a fluorescence sum component If$\lambda_+$, and a variable N/n=X, which represents the concentration of an extrinsic fluorescent molecule having been normalized with the concentration of an intrinsic fluorescent molecule.

Since C is a constant term, $If\lambda_1/If\lambda_+$ follows the curve shown in FIG. 3. Specifically, the non-uniformity $I\lambda_{ex}$ of the irradiance of the excitation light, depending upon sites, is canceled. The value of X represents the concentration of the extrinsic fluorescent molecule having been normalized with the concentration of the intrinsic fluorescent molecule. A large value of $If\lambda_1/If\lambda_+$ indicates that the fluorescence producing site is located at a diseased part. In this manner, the diseased part can be detected specifically by carrying out the division of the extrinsic fluorescence component $If\lambda_1$ and the fluorescence sum component $If\lambda_+$ by each other. In cases where the fluorescence sum component $If\lambda_+$ is used as the denominator in the division, the value of the denominator can be kept large, and therefore the occurrence of an operation error due to division by a value of zero can be restricted. Accordingly, for example, if an image sensor is employed as each of the fluorescence detecting means 3 and the fluorescence detecting means 4, a fluorescence image, in which the intensity of fluorescence has been corrected, can be displayed as a visible image on the display means 6.

Figure 4:
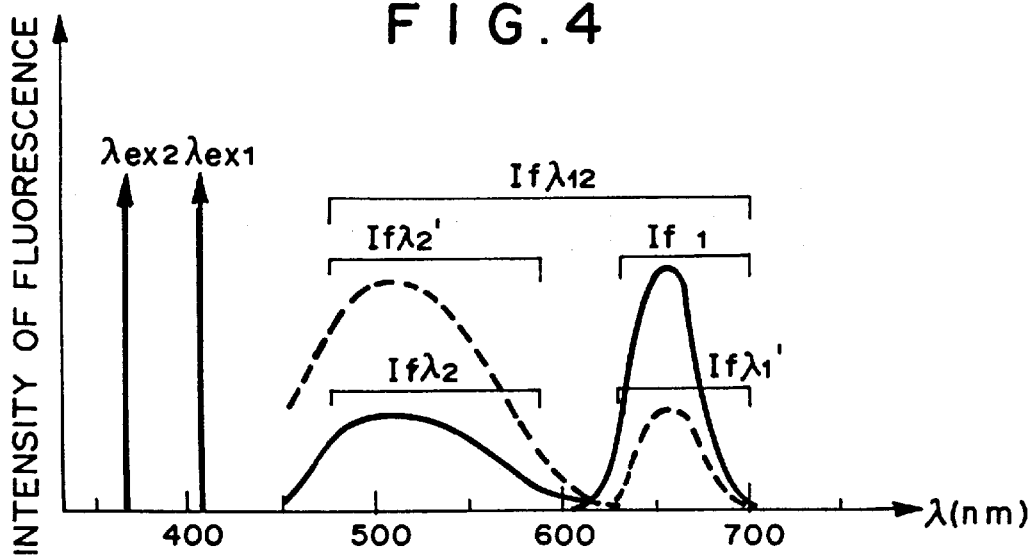
FIG. 4 is a graph showing the relationship between an intrinsic fluorescence component If$\lambda_2$, If$\lambda_2$' and an extrinsic fluorescence component If$\lambda_1$, If$\lambda_1$', which are obtained when light, that has wavelengths falling within a wavelength range in the vicinity of an excitation peak wavelength $\lambda_{ex1}$ for a fluorescent diagnosis drug, and light, that has wavelengths falling within a wavelength range in the vicinity of an excitation peak wavelength $\lambda_{ex2}$ for an intrinsic dye in a living body are employed as excitation light.

As an alternative to the excitation light described above, light, which has wavelengths falling within a wavelength range in the vicinity of an excitation peak wavelength $\lambda_{ex1}$ for the fluorescent diagnosis drug, and light, which has wavelengths falling within a wavelength range in the vicinity of an excitation peak wavelength $\lambda_{ex2}$ for the intrinsic dye in the living body may be employed as the excitation light. In such cases, the fluorescence having the spectrum illustrated in FIG. 4 can be obtained from the region of interest 10 in the living body. The symbols used herein for such cases have the meanings described below.

$If\lambda_1$: The contribution of the excitation light, which has a wavelength of $\lambda_{ex1}$, to the extrinsic fluorescence among the fluorescence produced from the region of interest in the living body.

$If\lambda_1'$: The contribution of the excitation light, which has a wavelength of $\lambda_{ex2}$, to the extrinsic fluorescence among the fluorescence produced from the region of interest in the living body.

$If\lambda_2$: The contribution of the excitation light, which has a wavelength of $\lambda_{ex1}$, to the intrinsic fluorescence among the fluorescence produced from the region of interest in the living body.

$If\lambda_2'$: The contribution of the excitation light, which has a wavelength of $\lambda_{ex2}$, to the intrinsic fluorescence among the fluorescence produced from the region of interest in the living body.

$I\lambda_{ex1}$: The intensity of the excitation light, which has a wavelength of $\lambda_{ex1}$, at the region of interest in the living body.

$I\lambda_{ex2}$: The intensity of the excitation light, which has a wavelength of $\lambda_{ex2}$, at the region of interest in the living body.

Also, in such cases, it is assumed that $I\lambda_{ex1}$ and $I\lambda_{ex2}$ are of the same distribution of light, and that $I\lambda_{ex2}=m \cdot I\lambda_{ex1}$ (where m is an arbitrary fixed number) at the region of interest in the living body.

In the same manner as that described above, fluorescence components having wavelengths falling within predetermined wavelength ranges are separated from each other. The extrinsic fluorescence component $If\lambda_1+If\lambda_1'$ is detected by the fluorescence detecting means 3, and the fluorescence sum component $If\lambda_+=If\lambda_1+If\lambda_1'+If\lambda_2+If\lambda_2'$ is detected by the fluorescence detecting means 4.

In such cases, $If\lambda_1$, $If\lambda_1'$, $If\lambda_2$, and $If\lambda_2'$ are represented by the formulas shown below.

$$If\lambda_1 = k_1\lambda_1 \cdot I\lambda_{ex1} \cdot \eta F\lambda_1 \cdot N \cdot \eta D$$

$$If\lambda_1' = k_1\lambda_1' \cdot I\lambda_{ex1}' \cdot \eta F\lambda_1' \cdot N \cdot \eta D$$

$$If\lambda_2 = k_2\lambda_2 \cdot I\lambda_{ex2} \cdot \eta F\lambda_2 \cdot n \cdot \eta D$$

$$If\lambda_2' = k_2\lambda_2' \cdot I\lambda_{ex2}' \cdot \eta F\lambda_2' \cdot n \cdot \eta D$$

The symbols used herein for such cases have the meanings described below.

$k_1\lambda_1$: The fixed number, which depends upon the wavelength $\lambda_{ex1}$ of the excitation light and the extrinsic fluorescent molecule.

$k_1\lambda_1'$: The fixed number, which depends upon the wavelength $\lambda_{ex2}$ of the excitation light and the extrinsic fluorescent molecule.

$\eta F\lambda_1$: The fluorescence quantum yield of the extrinsic fluorescent molecule with respect to the wavelength $\lambda_{ex1}$ of the excitation light.

$\eta F\lambda_1'$: The fluorescence quantum yield of the extrinsic fluorescent molecule with respect to the wavelength $\lambda_{ex2}$ of the excitation light.

$k_2\lambda_2$: The fixed number, which depends upon the wavelength $\lambda_{ex1}$ of the excitation light and the intrinsic fluorescent molecule.

$k_2\lambda_2'$: The fixed number, which depends upon the wavelength $\lambda_{ex2}$ of the excitation light and the intrinsic fluorescent molecule.

$\eta F\lambda_2$: The fluorescence quantum yield of the apparent intrinsic fluorescent molecule with respect to the wavelength $\lambda_{ex1}$ of the excitation light.

$\eta F\lambda_2'$: The fluorescence quantum yield of the apparent intrinsic fluorescent molecule with respect to the wavelength $\lambda_{ex2}$ of the excitation light.

Figure 5:
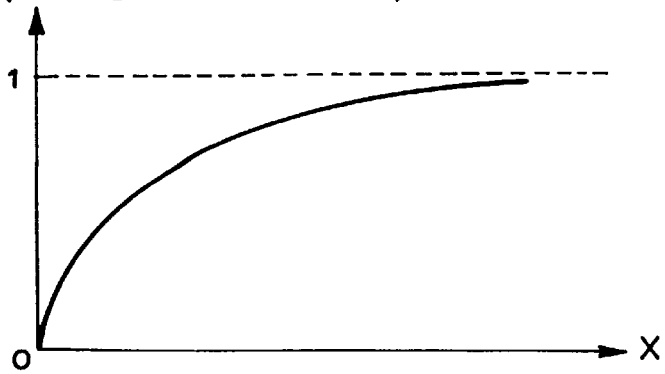
FIG. 5 is a graph showing the relationship between a quotient If$\lambda_1$/If$\lambda_+$=(If$\lambda_1$+If$\lambda_1$')/(If$\lambda_1$+If$\lambda_1$'+If$\lambda_2$+If$\lambda_2$'), which is obtained by dividing an extrinsic fluorescence component If$\lambda_1$ by a fluorescence sum component If$\lambda_+$, and a variable N/n=X, which represents the concentration of an extrinsic fluorescent molecule having been normalized with the concentration of an intrinsic fluorescent molecule.

Thereafter, the division means 5 carries out the division of the extrinsic fluorescence component $If\lambda_1+If\lambda_1'$ and the fluorescence sum component $If\lambda_++If\lambda_1=If\lambda_1'+If\lambda_2+If\lambda_2'$ by each other. The division yields the formula shown below.

$$(If\lambda_1+If\lambda_1')/(If\lambda_1+If\lambda_1'+If\lambda_2+If\lambda_2')=C\cdot X/(1+C\cdot X)$$

where $C=(k_1\lambda_1\cdot\eta F\lambda_1+k_1\lambda_1'\cdot m\cdot\eta F\lambda_1')/(k_2\lambda_2\cdot\eta F\lambda_2+k_2\lambda_2'\cdot m\cdot\eta F\lambda_2')$ $X=N/n$ Since C is a constant term, $(If\lambda_1+If\lambda_1')/(If\lambda_1+If\lambda_1'+If\lambda_2+If\lambda_2')$ follows the curve shown in FIG. 5. Specifically, the non-uniformity $I\lambda_{ex1}$ and the non-uniformity $I\lambda_{ex2}$ of the irradiance of the excitation light, depending upon sites, are canceled. The value of X represents the concentration of the extrinsic fluorescent molecule having been normalized with the concentration of the intrinsic fluorescent molecule. A large value of $(If\lambda_1+If\lambda_1')/(If\lambda_1+If\lambda_1'+If\lambda_2+If\lambda_2')$ indicates that the fluorescence producing site is located at a diseased part.

Therefore, in such cases, the fluorescence produced from the diseased part can be specifically detected as an image by carrying out the division of the fluorescence image, which is obtained in accordance with the extrinsic fluorescence component $If\lambda_1+If\lambda_1'$, and the fluorescence image, which is obtained in accordance with the fluorescence sum component $If\lambda_+$, by each other. In this manner, the diseased part can be detected specifically by carrying out the division of the extrinsic fluorescence component $If\lambda_1+If\lambda_1'$ and the fluorescence sum component $If\lambda_+$ by each other, in cases where the fluorescence sum component $If\lambda_+$ is used as the denominator in the division, the value of the denominator can be kept large, and therefore the occurrence of an operation error due to division by a value of zero can be restricted. Accordingly, for example, if an image sensor is employed as each of the fluorescence detecting means 3 and the fluorescence detecting means 4, a fluorescence image, in which the intensity of fluorescence has been corrected, can be displayed as a visible image on the display means 6. Also, in cases where the light, which has wavelengths falling within a wavelength range in the vicinity of an excitation peak wavelength $\lambda_{ex1}$ for the fluorescent diagnosis drug, and the light, which has wavelengths falling within a wavelength range in the vicinity of an excitation peak wavelength $\lambda_{ex2}$ for the intrinsic dye in the living body are thus employed as the excitation light, the intensity of fluorescence can be kept sufficiently high, and a fluorescence image having good image quality with a high signal-to-noise ratio can be obtained.

The constitution described above is designed for the cases where the fluorescence with the administration of the drug is detected, and the extrinsic fluorescence component and the fluorescence sum component, which is the sum of the extrinsic fluorescence component and the intrinsic fluorescence component, are divided by each other. A constitution described below is designed for the fluorescence detecting apparatus, wherein the intrinsic fluorescence produced from the region of interest in the living body, to which no fluorescent diagnosis drug has been administered, is detected. (Such cases will hereinbelow be referred to as "cases where the autofluorescence without the administration of the drug is detected.") In such cases, the excitation light is irradiated to the region of interest in the living body, to which no fluorescent diagnosis drug has been administered. When the region of interest in the living body is exposed to the excitation light, the intrinsic fluorescence is produced by the intrinsic dye in the region of interest in the living body. A fluorescence component (for example, a red region component R: hereinbelow referred to as the "long wavelength component"), which has wavelengths falling within a comparatively long wavelength range among the wavelength range of the intrinsic fluorescence having been produced by the intrinsic dye in the living body, is detected from the intrinsic fluorescence. Also, a fluorescence sum component, which is the sum of the long wavelength component and a fluorescence component (for example, a green region component G: hereinbelow referred to as the "short wavelength component"), that has wavelengths falling within a comparatively short wavelength range among the wavelength range of the intrinsic fluorescence having been produced by the intrinsic dye in the living body, is detected. The long wavelength component and the fluorescence sum component are then divided by each other. The constitution will hereinbelow be described in detail.

In this constitution, as in the aforesaid cases where the fluorescence with the administration of the drug is detected, the intrinsic fluorescence L3, which is produced by the intrinsic dye in the region of interest 10 in the living body, is separated with respect to wavelength ranges by a dichroic mirror, an optical filter, or the like. A long wavelength component $If\lambda_1$ and a fluorescence sum component $If\lambda_+$, which is the sum of the long wavelength component $If\lambda_1$ and a short wavelength component $If\lambda_2$, are thereby separated from each other. The fluorescence detecting means 3 detects the long wavelength component among the intrinsic fluorescence L3, which has been produced by the intrinsic dye in the region of interest 10 in the living body. The fluorescence detecting means 4 detects the fluorescence sum component among the intrinsic fluorescence L3, which has been produced by the intrinsic dye in the region of interest 10 in the living body. The other features are the same as those in the aforesaid cases where the fluorescence with the administration of the drug is detected. The means for detecting the long wavelength component and the means for detecting the fluorescence sum component are not limited to those employed in this constitution. As an alternative, fluorescence components having wavelengths falling within predetermined wavelength ranges may be separated from each other and detected, and a fluorescence component having wavelengths falling within a wavelength range to be used ultimately may be calculated by carrying out an operation, such as addition or subtraction, on the results of the detection. For example, the fluorescence L3 may be separated with respect to wavelength ranges, and the long wavelength component and the short wavelength component may thereby be separated from each other. Thereafter, the long wavelength component may be detected by the fluorescence detecting means 3, and the short wavelength component may be detected by the fluorescence detecting means 4. The outputs obtained from the fluorescence detecting means 3 and the fluorescence detecting means 4 may then be added to each other, and the fluorescence sum component may thereby be obtained. As another alternative, the fluorescence L3 may be separated with respect to wavelength ranges, and the short wavelength component and the fluorescence sum component, which is the sum of the long wavelength component and the short wavelength component, may thereby be separated from each other. Also, the short wavelength component may be detected by the fluorescence detecting means 3, and the fluorescence sum component may be detected by the fluorescence detecting means 4. Thereafter, the short wavelength component may be subtracted from the fluorescence sum component, and the long wavelength component may thereby be obtained.

Figure 19:
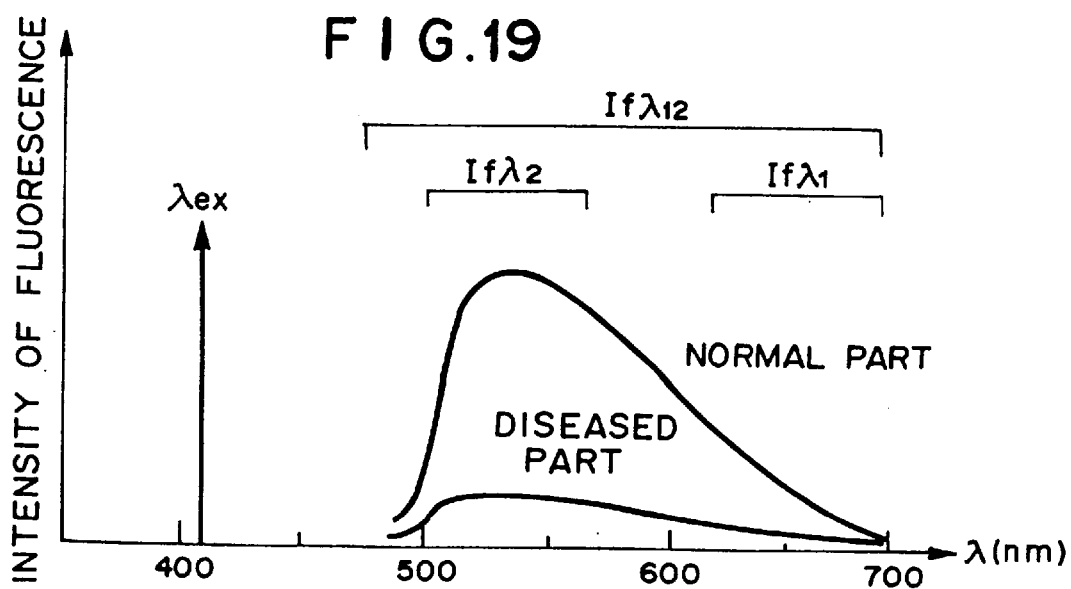
FIG. 19 is a graph showing optical characteristics of a dichroic mirror employed in the fifth embodiment.

How the fluorescence detecting apparatus having this constitution operates will be described hereinbelow. When the excitation light L1 is irradiated to the region of interest 10 in the living body, the region of interest 10 in the living body is excited by the excitation light L1 and produces the intrinsic fluorescence L3 having a spectrum illustrated in FIG. 19. It is assumed that the intrinsic fluorescence L3 comprises the fluorescence produced by various kinds of intrinsic dyes in the living body, such as FAD, collagen, fibronectin, and porphyrin. As illustrated in FIG. 19, the level and the pattern of the spectrum of the fluorescence vary for the normal part and the diseased part. The level of the intrinsic fluorescence L3 produced from the normal part is high as a whole, and the level of the intrinsic fluorescence L3 produced from the diseased part is low as a whole. Also, in particular, as for the intrinsic fluorescence L3, which is obtained from the diseased part, the degree of reduction in the level of the fluorescence component having wavelengths longer than the wavelength of the red color, as compared with the level of the fluorescence component, which is of the intrinsic fluorescence L3 obtained from the normal part and has wavelengths longer than the wavelength of the red color, is smaller than the degree of reduction in the level of the fluorescence component of the blue to green region, as compared with the level of the fluorescence component, which is of the blue to green region in the intrinsic fluorescence L3 obtained from the normal part. (The reason why the fluorescence spectrum varies for the diseased part and the normal part has not yet been clarified completely.) Specifically, the ratio of the fluorescence component in the vicinity of the red color (i.e., the long wavelength component) If$\lambda_1$ and the fluorescence component in the vicinity of the green color (i.e., the short wavelength component) If$\lambda_2$ to each other varies for the diseased part and the normal part. Therefore, it can be judged that a site associated with a large value of quotient If$\lambda_1$/If$\lambda_2$ is the one belonging to the diseased part, and that a site associated with a small value of quotient If$\lambda_1$/If$\lambda_2$ is the one belonging to the normal part. The respective wavelength components may be represented as described below.

The apparent long wavelength component If$\lambda_1$, which is obtained when the excitation light L1 is irradiated to the region of interest 10 in the living body, may be represented by the formula shown below.

$$If\lambda_1 = k\lambda_1 \cdot I\lambda_{ex} \cdot \eta F\lambda_1 \cdot n \cdot \eta D$$

The apparent short wavelength component If$\lambda_2$, which is obtained when the excitation light L1 is irradiated to the region of interest 10 in the living body, may be represented by the formula shown below.

$$If\lambda_2 = k\lambda_2 \cdot I\lambda_{ex} \cdot \eta F\lambda_2 \cdot N \cdot \eta D$$

Therefore, the fluorescence sum component If$\lambda_+$, which is the sum of the long wavelength component and the short wavelength component, may be represented by the formula shown below.

$$If\lambda_+ = (k\lambda_1 \cdot I\lambda_{ex} \cdot \eta F\lambda_1 \cdot n \cdot \eta D) + (k\lambda_2 \cdot I\lambda_{ex} \cdot \eta F\lambda_2 \cdot N \cdot \eta D)$$

Unless otherwise specified, the symbols used herein for the cases where the autofluorescence without the administration of the drug is detected have the meanings described below. This also applies to the below-described cases where the autofluorescence without the administration of the drug is detected.

$\lambda_{ex}$: The wavelength of the excitation light.

$I\lambda_{ex}$: The intensity of the excitation light at the region of interest in the living body, which intensity depends upon the distance L between the excitation light source and the region of interest in the living body, the power P of the excitation light source, and the angle $\theta$ made between the excitation light beam and the region of interest in the living body. $I\lambda_{ex} = I\lambda_{ex}(L, P, \theta)$ n: The concentration of the apparent intrinsic fluorescent molecule, which contributes to the fluorescence having wavelengths falling within the long wavelength range. (It is considered that a plurality of kinds of fluorescent molecules contributing to the intrinsic fluorescence are present in the living body. They can virtually be processed such that only a single kind of molecule may be present, and therefore the term "apparent" is used herein.)

N: The concentration of the apparent intrinsic fluorescent molecule, which contributes to the fluorescence having wavelengths falling within the short wavelength range.

M: The concentration of the apparent intrinsic fluorescent molecule, which contributes to the fluorescence having wavelengths falling within the entire wavelength range.

$k\lambda_1$: The fixed number, which depends upon the wavelength $\lambda_{ex}$ of the excitation light and the apparent intrinsic fluorescent molecule, which contributes to the fluorescence having wavelengths falling within the long wavelength range.

$k\lambda_2$: The fixed number, which depends upon the wavelength $\lambda_{ex}$ of the excitation light and the apparent intrinsic fluorescent molecule, which contributes to the fluorescence having wavelengths falling within the short wavelength range.

$k\lambda_{12}$: The fixed number, which depends upon the wavelength $\lambda_{ex}$ of the excitation light and the apparent intrinsic fluorescent molecule, that contributes to the fluorescence having wavelengths falling within the entire wavelength range.

$\eta F\lambda_1$: The fluorescence quantum yield of the apparent intrinsic fluorescent molecule, which contributes to the fluorescence having wavelengths falling within the long wavelength range, with respect to the wavelength $\lambda_{ex}$ of the excitation light.

$\eta F\lambda_2$: The fluorescence quantum yield of the apparent intrinsic fluorescent molecule, which contributes to the fluorescence having wavelengths falling within the short wavelength range, with respect to the wavelength $\lambda_{ex}$ of the excitation light.

$\eta F\lambda_{12}$: The fluorescence quantum yield of the apparent intrinsic fluorescent molecule, which contributes to the fluorescence having wavelengths falling within the entire wavelength range, with respect to the wavelength $\lambda_{ex}$ of the excitation light.

$\eta D$: The fluorescence detection efficiency, which depends upon the distance L' between the fluorescence producing site and the fluorescence receiving optical system, the size D of the aperture of the fluorescence receiving optical system, and the efficiency ξ of the photo detecting device. ηD=ηD (L', ξ, D). (In the strict sense, the detection efficiency with respect to the fluorescence, which has wavelengths falling within the short wavelength range, and the detection efficiency with respect to the fluorescence, which has wavelengths falling within the long wavelength range, are different from each other. However, they can herein be processed as being approximately equal to each other.)

Thereafter, the division means 5 carries out the division of the long wavelength component If$\lambda_1$ and the fluorescence sum component If$\lambda_+$(=If$\lambda_1$+If$\lambda_2$) by each other. The quotient of the division If$\lambda_1$/(If$\lambda_1$+If$\lambda_2$) may be represented by the formula shown below.

$$If\lambda_1/(If\lambda_1 + If\lambda_2) = (k\lambda_1 \cdot \eta F\lambda_1 \cdot n)/(k\lambda_1 \cdot \eta F\lambda_1 \cdot n + k\lambda_2 \cdot \eta F\lambda_2 \cdot N)$$

By this division, the non-uniformity I$\lambda_{ex}$ of the irradiance of the excitation light, depending upon sites, is canceled. Therefore, in this constitution wherein the long wavelength component (for example, the red region component R), which is among the intrinsic fluorescence, and the fluorescence sum component (for example, G+R), which is the sum of the short wavelength component (for example, the green region component G) and the long wavelength component, are divided by each other, in cases where the fluorescence sum component If$\lambda_+$ is used as the denominator in the division, the value of the denominator can be kept large, and therefore the occurrence of an operation error due to division by a value of zero can be restricted. Accordingly, for example, if an image sensor is employed as each of the fluorescence detecting means 3 and the fluorescence detecting means 4, a fluorescence image, in which the intensity of fluorescence has been corrected, can be displayed as a visible image on the display means 6.

The fluorescence detecting apparatus in accordance with the present invention is also applicable when a fluorescence difference component and the fluorescence sum component are divided by each other. A constitution described below is designed for the cases where the fluorescence with the administration of the drug is detected. Also, in this constitution, a fluorescence difference component (In−Ex), which is the difference between the intrinsic fluorescence In and the extrinsic fluorescence component Ex, and the fluorescence sum component (In+Ex), which is the sum of the intrinsic fluorescence component In and the extrinsic fluorescence component Ex, are divided by each other. The constitution will hereinbelow be described in detail.

In this constitution, as in the aforesaid cases where the fluorescence with the administration of the drug is detected, the fluorescence L3, which has been produced from the region of interest 10 in the living body, is received by the fluorescence receiving optical system 2. The fluorescence L3 is separated with respect to wavelength ranges by a dichroic mirror, an optical filter, or the like. The fluorescence difference component, which is the difference between the intrinsic fluorescence and the extrinsic fluorescence component having been produced from the region of interest 10 in the living body, and the fluorescence sum component, which is the sum of the intrinsic fluorescence component and the extrinsic fluorescence component, are thereby separated from each other. The fluorescence detecting means 3 detects the fluorescence difference component, and the fluorescence detecting means 4 detects the fluorescence sum component. The other features are the same as those in the aforesaid cases where the fluorescence with the administration of the drug is detected. The wavelength range of the intrinsic fluorescence component, which is used in the detection of the fluorescence difference component, and the wavelength range of the intrinsic fluorescence component, which is contained in the fluorescence sum component, need not necessarily be identical with each other. Also, the wavelength range of the extrinsic fluorescence component, which is used in the detection of the fluorescence difference component, and the wavelength range of the extrinsic fluorescence component, which is contained in the fluorescence sum component, need not necessarily be identical with each other. Further, as in the aforesaid cases, the means for detecting the fluorescence difference component and the means for detecting the fluorescence sum component are not limited to those employed in this constitution. As an alternative, fluorescence components having wavelengths falling within predetermined wavelength ranges may be separated from each other and detected, and a fluorescence component having wavelengths falling within a wavelength range to be used ultimately may be calculated by carrying out an operation, such as addition or subtraction, on the results of the detection. How the fluorescence detecting apparatus having the constitution described above operates will be described hereinbelow.

The wavelength components detected by the fluorescence detecting means 3 and the fluorescence detecting means 4 may be represented as described below. As will be clear from the foregoing, the fluorescence sum component If$\lambda_+$ may be represented by the formula shown below.

$$If\lambda_+ = If\lambda_2 + If\lambda_1$$
$$= (k\lambda_2 \cdot I\lambda_{ex} \cdot \eta F\lambda_2 \cdot n \cdot \eta D) +$$
$$(k\lambda_1 \cdot I\lambda_{ex} \cdot \eta F\lambda_1 \cdot N \cdot \eta D)$$

The fluorescence difference component If$\lambda_-$ may be represented by the formula shown below:

$$If\lambda_- = If\lambda_2 - If\lambda_1$$
$$= (k\lambda_2 \cdot I\lambda_{ex} \cdot \eta F\lambda_2 \cdot n \cdot \eta D) -$$
$$(k\lambda_1 \cdot I\lambda_{ex} \cdot \eta F\lambda_1 \cdot N \cdot \eta D)$$

Thereafter, the division means 5 carries out the division of the fluorescence difference component If$\lambda_-$ and the fluorescence sum component If$\lambda_+$ by each other. The division may be represented by the formula shown below.

$$If\lambda_-/If\lambda_+ = (k\lambda_2 \cdot I\lambda_{ex} \cdot \eta F\lambda_2 \cdot n \cdot \eta D) -$$
$$(k\lambda_1 \cdot I\lambda_{ex} \cdot \eta F\lambda_1 \cdot N \cdot \eta D)/$$
$$(k\lambda_2 \cdot I\lambda_{ex} \cdot \eta F\lambda_2 \cdot n \cdot \eta D) +$$
$$(k\lambda_1 \cdot I\lambda_{ex} \cdot \eta F\lambda_1 \cdot N \cdot \eta D)$$
$$= (k\lambda_2 \cdot \eta F\lambda_2 \cdot n - k\lambda_1 \cdot \eta F\lambda_1 \cdot N)/$$
$$(k\lambda_2 \cdot \eta F\lambda_2 \cdot n + k\lambda_1 \cdot \eta F\lambda_1 \cdot N)$$

If $(k\lambda_1 \cdot \eta F\lambda_1)/(k\lambda_2 \cdot \eta F\lambda_2) = C$ and $N/n = X$, the formula shown below will obtain.

$$If\lambda_-/If\lambda_+ = (1 - C \cdot X)/(1 + C \cdot X)$$

Specifically, in this constitution, the non-uniformity I$\lambda_{ex}$ of the irradiance of the excitation light, depending upon sites, is canceled. The value of X represents the concentration of the extrinsic fluorescent molecule having been normalized with the concentration of the intrinsic fluorescent molecule. A large value of $If\lambda_-/If\lambda_+$ indicates that the extrinsic fluorescence is weak and that the fluorescence producing site is located at the normal part. Conversely, a small value of $If\lambda_-/If\lambda_+$ indicates that the extrinsic fluorescence is strong and that the fluorescence producing site is located at the diseased part. In this manner, the diseased part can be detected specifically by carrying out the division of the fluorescence difference component $If\lambda_-$ and the fluorescence sum component $If\lambda_+$ by each other. In cases where the fluorescence sum component $If\lambda_+$ is used as the denominator in the division, the value of the denominator can be kept large, and therefore the occurrence of an operation error due to division by a value of zero can be restricted.

The constitution described above is designed for the cases where the fluorescence with the administration of the drug is detected. The same idea as that of the constitution described above is also applicable to the cases where the autofluorescence without the administration of the drug is detected. In this constitution, the fluorescence difference component in the fundamental constitution 3 may be replaced by a fluorescence difference component (for example, G–R), which is the difference between the short wavelength component (for example, the green region component G) and the long wavelength component (for example, the red region component R). Also, the fluorescence sum component in the fundamental constitution 3 may be replaced by the fluorescence sum component (for example, G+R), which is the sum of the short wavelength component (for example, the green region component G) and the long wavelength component (for example, the red region component R).

In the constitutions described above, the fluorescence sum component is employed in the division. The fluorescence detecting apparatus in accordance with the present invention is also applicable when a fluorescence component (i.e., an entire fluorescence component), which has wavelengths falling within approximately the entire wavelength range of the fluorescence, that is produced from the region of interest 10 in the living body when the region of interest 10 is exposed to the excitation light, is employed in the division. Constitutions for such cases will hereinbelow be described in detail.

A constitution described below is designed for the cases where the autofluorescence without the administration of the drug is detected. In this constitution, the fluorescence difference component (for example, G–R), which is the difference between the short wavelength component (for example, the green region component G) and the long wavelength component (for example, the red region component R), and an entire fluorescence component are divided by each other.

As in the constitutions described above, wherein the fluorescence sum component is employed in the division, the intrinsic fluorescence L3, which is produced from the region of interest 10 in the living body, is received by the fluorescence receiving optical system 2. The intrinsic fluorescence L3 is separated with respect to wavelength ranges by a dichroic mirror, an optical filter, or the like. A fluorescence difference component $If\lambda_-$, which is the difference between the short wavelength component $If\lambda_2$ and the long wavelength component $If\lambda_1$, and an entire fluorescence component $If\lambda_{12}$, which contains the short wavelength component $If\lambda_2$ and the long wavelength component $If\lambda_1$, are thereby separated from each other. The fluorescence detecting means 3 detects the fluorescence difference component $If\lambda_-$, and the fluorescence detecting means 4 detects the entire fluorescence component $If\lambda_{12}$. The other features are the same as those in the aforesaid constitutions. As in the aforesaid constitutions, the means for detecting the fluorescence difference component and the means for detecting the entire fluorescence component are not limited to those employed in this constitution. In particular, the means for detecting the entire fluorescence component may be constituted in the manner described below. Specifically, the characteristics of wavelength separation between the short wavelength component and the long wavelength component may be devised specifically (such that, for example, the cut-off characteristics on the long-wavelength side of the short wavelength component and the cut-off characteristics on the short-wavelength side of the long wavelength component may be identical with each other), and the short wavelength component and the long wavelength component may thereby be separated from each other and detected. The results of the detection may then be added to each other, and a fluorescence sum component may thereby be obtained. The thus obtained fluorescence sum component may be employed as the entire fluorescence component. In such cases, the constitution for carrying out the division using the fluorescence sum component described above can directly function as the constitution for carrying out the division using the entire fluorescence component. Such means for detecting the entire fluorescence component may also be employed in the constitutions described later.

How the fluorescence detecting apparatus having the fundamental constitution 5 described above operates will be described hereinbelow. The wavelength components detected by the fluorescence detecting means 3 and the fluorescence detecting means 4 may be represented as described below. As will be clear from the foregoing, the fluorescence difference component $If\lambda_-$ may be represented by the formula shown below.

$$If\lambda_- = If\lambda_2 - If\lambda_1$$
$$= (k\lambda_2 \cdot I\lambda_{ex} \cdot \eta F\lambda_2 \cdot N \cdot \eta D) -$$
$$(k\lambda_1 \cdot I\lambda_{ex} \cdot \eta F\lambda_1 \cdot n \cdot \eta D)$$

The entire fluorescence component $If\lambda_{12}$ having wavelengths falling within the wavelength range, which contains the short wavelength range and the long wavelength range, may be represented by the formula shown below.

$$If\lambda_{12} = k\lambda_{12} \cdot I\lambda_{ex} \cdot \eta F\lambda_{12} \cdot M \cdot \eta D$$

Thereafter, the division means 5 carries out the division of the fluorescence difference component $If\lambda_-$ and the entire fluorescence component $If\lambda_{12}$ by each other. The division may be represented by the formula shown below.

$$If\lambda_- / If\lambda_{12} = (k\lambda_2 \cdot I\lambda_{ex} \cdot \eta F\lambda_2 \cdot N \cdot \eta D) -$$
$$(k\lambda_1 \cdot I\lambda_{ex} \cdot \eta F\lambda_1 \cdot n \cdot \eta D)/$$
$$(k\lambda_{12} \cdot I\lambda_{ex} \cdot \eta F\lambda_{12} \cdot M \cdot \eta D)$$
$$= k\lambda_2 \cdot \eta F\lambda_2 \cdot N / k\lambda_{12} \cdot \eta F\lambda_{12} \cdot M -$$
$$k\lambda_1 \cdot \eta F\lambda_1 \cdot n / k\lambda_{12} \cdot \eta F\lambda_{12} \cdot M$$
$$= (C_1/M) \cdot (N - C_2 \cdot M)$$

where each of $C_1$ and $C_2$ is a fixed number.

Specifically, in this constitution, the non-uniformity $I\lambda_{ex}$ of the irradiance of the excitation light, depending upon sites, is canceled. A large value of $If\lambda_-/If\lambda_{12}$ indicates that the fluorescence having wavelengths falling within the short wavelength range is strong and that the fluorescence producing site is located at the normal part. Conversely, a small value of If$\lambda_-$/If$\lambda_{12}$ indicates that the fluorescence having wavelengths falling within the short wavelength range is weak and that the fluorescence producing site is located at the diseased part. In this manner, the diseased part can be detected specifically by carrying out the division of the fluorescence difference component If$\lambda_-$ and the entire fluorescence component If$\lambda_{12}$ by each other. In cases where the entire fluorescence component If$\lambda_{12}$ is used as the denominator in the division, the value of the denominator can be kept large, and therefore the occurrence of an operation error due to division by a value of zero can be restricted.

The constitution described above is designed for the cases where the autofluorescence without the administration of the drug is detected, and the fluorescence difference component (for example, G–R), which is the difference between the short wavelength component (for example, the green region component G) and the long wavelength component (for example, the red region component R), and the entire fluorescence component are divided by each other. The same idea as that in the constitution described above is also applicable when the long wavelength component (for example, the red region component R) and the entire fluorescence component are divided by each other. In such cases, the fluorescence difference component in the constitution described above may be replaced by the long wavelength component.

The two last-described constitutions are designed for the cases where the autofluorescence without the administration of the drug is detected. The same ideas as those in the two last-described constitutions are also applicable to the cases where the fluorescence with the administration of the drug is detected. In such cases, the division of the fluorescence difference component and the entire fluorescence component by each other in the constitution described above may be replaced by the division of the fluorescence difference component (In–Ex), which is the difference between the intrinsic fluorescence component In and the extrinsic fluorescence component Ex, and the entire fluorescence component by each other. Also, the division of the long wavelength component and the entire fluorescence component by each other in the constitution described above may be replaced by the division of the extrinsic fluorescence component Ex and the entire fluorescence component by each other.

Embodiments of the fluorescence detecting apparatus in accordance with the present invention will be described hereinbelow.

Figure 6:
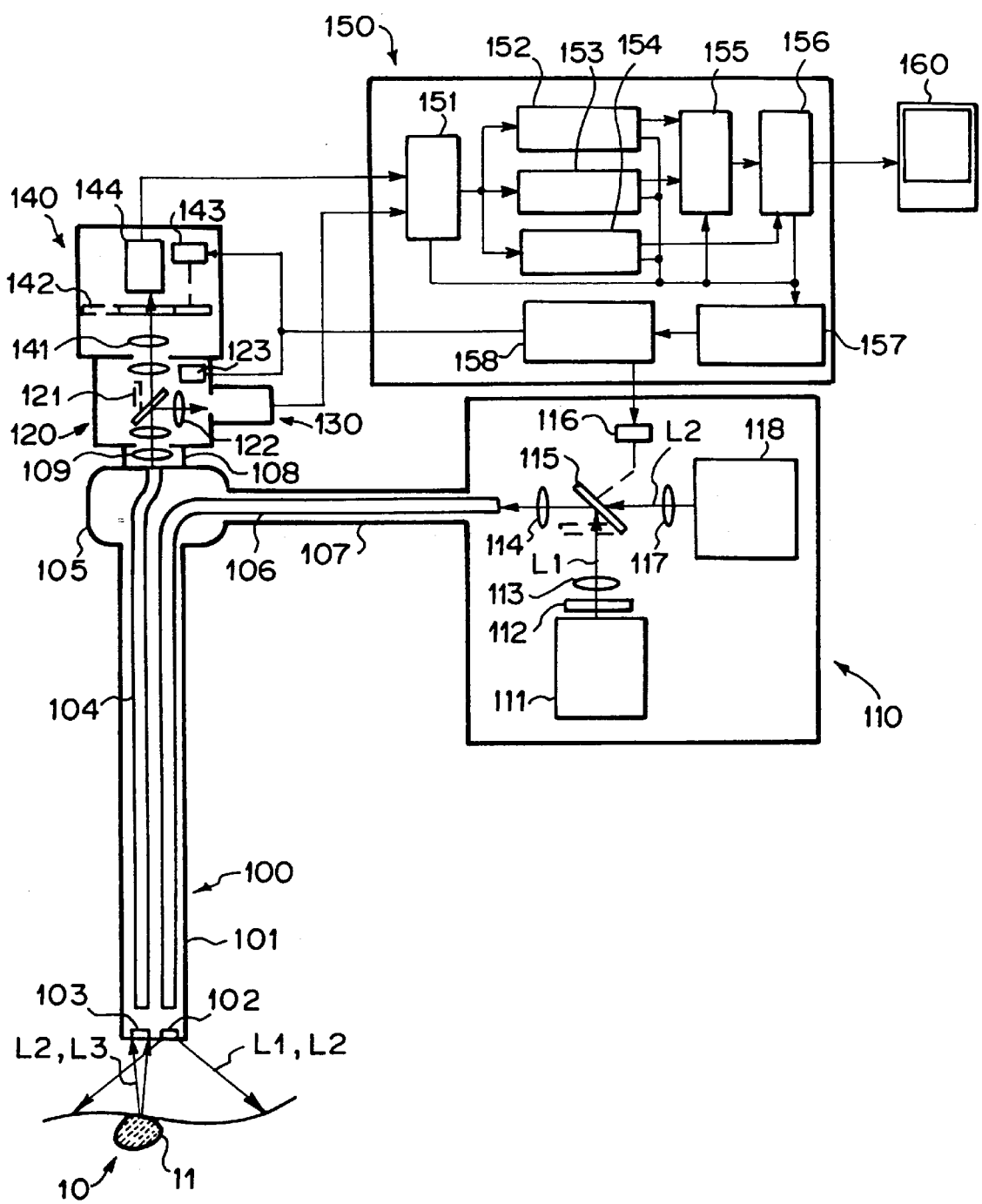
FIG. 6 is a schematic view showing an endoscope system, in which a first embodiment of the fluorescence detecting apparatus in accordance with the present invention is employed.

FIG. 6 is a schematic view showing an endoscope system, in which a first embodiment of the fluorescence detecting apparatus in accordance with the present invention is employed. In the endoscope system, excitation light is irradiated to a region of interest in a living body, to which a fluorescent diagnosis drug has been administered, and fluorescence, which is produced from the region of interest in the living body when the region of interest is exposed to the excitation light, is detected. Also, an extrinsic fluorescence component and an entire fluorescence component, which contains an intrinsic fluorescence component and the extrinsic fluorescence component, are divided by each other.

The endoscope system, in which the first embodiment of the fluorescence detecting apparatus in accordance with the present invention is employed, comprises an endoscope 100 to be inserted into a site of a patient, which site is considered as being a diseased part, and an illuminating device 110 provided with light sources for producing white light, which is used when an ordinary image is to be obtained, and the excitation light, which is used when a fluorescence image is to be obtained. The endoscope system also comprises an optical path change-over unit 120, which changes an optical path for obtaining the ordinary image, and an optical path for obtaining the fluorescence image, over to each other. The endoscope system further comprises a color CCD camera 130 for detecting the white light, which is reflected from a region of interest 10 in the living body when the ordinary image is to be obtained, and a high-sensitivity camera unit 140 for detecting the fluorescence, which is produced from the region of interest 10 in the living body when the fluorescence image is to be obtained. The endoscope system still further comprises an image processing unit 150 for carrying out image processing on an image signal, which represents the reflected light image or the fluorescence image having been detected, and a display device 160 for reproducing a visible image from the image signal, which has been obtained from the image processing carried out by the image processing unit 150, and displaying the reproduced visible image.

The endoscope 100 is provided with an endoscope tube 101, which is to be inserted into the living body. A light guide 106 and an image fiber 104 extend in the endoscope tube 101 up to a leading end of the endoscope tube 101. An illuminating lens 102 is located at a leading end of the light guide 106, i.e. at the leading end of the endoscope tube 101. An objective lens 103 is located at a leading end of the image fiber 104, i.e. at the leading end of the endoscope tube 101. A tail end portion of the light guide 106 passes through a connecting section 107 for connecting the illuminating device 110 and a manipulating section 105 to each other and extends into the illuminating device 110. A tail end portion of the image fiber 104 extends in the manipulating section 105, and its tail end is in contact with an eyepiece section 108, which is provided with an eyepiece 109.

The illuminating device 110 comprises a xenon lamp 118 for producing the white light L2 for obtaining the ordinary image, and a mercury vapor lamp 111 for producing the excitation light L1 for obtaining the fluorescence image. The illuminating device 110 also comprises an optical filter 112 for setting the transmission wavelength of the excitation light L1 having been produced by the mercury vapor lamp 111, and a change-over mirror 115, which is operated by a driver 116 and changes the white light L2 for obtaining the ordinary image and the excitation light L1 for obtaining the fluorescence image over to each other.

The optical path change-over unit 120 is provided with a change-over mirror 121, which is operated by a driver 123. The change-over mirror 121 changes the optical paths over to each other such that the reflected white light L2 having passed through the image fiber 104 may impinge upon the color CCD camera 130 when the ordinary image is to be obtained, or such that the fluorescence L3 having passed through the image fiber 104 may enter into the high-sensitivity camera unit 140 when the fluorescence image is to be obtained.

The high-sensitivity camera unit 140 comprises a change-over optical filter 142 for transmitting the fluorescence L3, which has passed through the image fiber 104 when the fluorescence image is to be obtained. As illustrated in FIG. 7, the change-over optical filter 142 is provided with a sharp cut filter 142a, which transmits entire fluorescence, and a sharp cut filter 142b, which transmits extrinsic fluorescence, such that the two sharp cut filters may be changed over to each other. The high-sensitivity camera unit 140 also comprises a cold CCD camera, on which an image of the fluorescence L3 having passed through the change-over optical filter 142 is formed. The sharp cut filter 142a, which transmits the entire fluorescence, and the sharp cut filter 142b, which transmits the extrinsic fluorescence, of the change-over optical filter 142 are changed over to each other by a driver 143.

The image processing unit 150 comprises an analog-to-digital conversion circuit 151 for digitizing the image signals having been obtained from the CCD cameras. The image processing unit 150 also comprises an ordinary image memory 154 for storing a digitized ordinary image signal, and an extrinsic fluorescence image memory 152 for storing a digitized image signal, which represents an extrinsic fluorescence component. The image processing unit 150 further comprises an entire fluorescence image memory 153 for storing a digitized image signal, which represents the entire fluorescence, and a division memory 155 for carrying out division of the extrinsic fluorescence component and the entire fluorescence component by each other and storing the information representing the results of the division. The image processing unit 150 still further comprises a video signal forming circuit 156 for carrying out image processing on the image signal, which is received from the ordinary image memory 154 or the division memory 155, and thereby obtaining a video signal to be used for reproducing the visible image on the display device 160. The image processing unit 150 also comprises a timing controller 158 for feeding signals into the driver 116, which drives the change-over mirror 115 of the illuminating device 110, the driver 123, which drives the change-over mirror 121 of the optical path change-over unit 120, and the driver 143, which drives the change-over optical filter 142 of the high-sensitivity camera unit 140. The image processing unit 150 further comprises a video processor 157 for controlling the timing controller 158.

How the endoscope system, in which the first embodiment of the fluorescence detecting apparatus in accordance with the present invention is employed, operates will be described hereinbelow. Firstly, how the endoscope system operates when the ordinary image is to be obtained will be described hereinbelow.

When the ordinary image is to be obtained, the change-over mirror 115 of the illuminating device 110 is driven by the driver 116 in accordance with the signal fed from the timing controller 158 and is moved to the position indicated by the broken line in FIG. 6, such that the change-over mirror 115 may not obstruct the travel of the white light L2. The white light L2 having been produced by the xenon lamp 118 passes through a lens 117 and travels to the change-over mirror 115. The white light L2 is caused by a lens 114 to enter into the light guide 106, guided through the light guide 106 to the leading end of the endoscope 100, and then irradiated through the illuminating lens 102 to the region of interest 10 in the living body, which contains the diseased part 11. The white light L2, which has been reflected from the region of interest 10 in the living body, is collected by the objective lens 103 and passes through the image fiber 104 and the eyepiece 109, which is located in the eyepiece section 108. The reflected white light L2 then travels to the change-over mirror 121, which is located in the optical path change-over unit 120. The change-over mirror 121 is driven by the driver 123 in accordance with the signal fed from the timing controller 158 and is moved to the position indicated by the solid line in FIG. 6 when the ordinary image is to be obtained. The reflected white light L2 is reflected by the change-over mirror 121. A lens 122 forms the image of the reflected white light L2 on the color CCD camera 130. The image signal obtained from the color CCD camera 130 is fed into the analog-to-digital conversion circuit 151. The analog-to-digital conversion circuit 151 digitizes each of R, G, and B image signals, and the thus obtained digital R, G, and B image signals are stored in the ordinary image memory 154 corresponding to R,G, and B images. The ordinary image signals are then fed into the video signal forming circuit 156. In the video signal forming circuit 156, the ordinary image signals are subjected to digital-to-analog conversion, color matrix processing, and encoding. The ordinary image signals having been obtained from the processing are then fed as NTSC signals into the display device 160. The display device 160 reproduces the visible image from the signals and displays it.

How the endoscope system operates when the fluorescence image is to be obtained will be described hereinbelow. In this embodiment, ATX-S10 capable of producing the fluorescence having a wavelength of approximately $\lambda_{em}$= 670 nm is employed as the fluorescent diagnosis drug. The fluorescent diagnosis drug ATX-S10 has been administered to the region of interest 10 in the living body.

The change-over mirror 115 of the illuminating device 110 is driven by the driver 116 in accordance with the signal fed from the diming controller 158 and is moved to the position indicated by the solid line in FIG. 6, such that the change-over mirror 115 may block the travel of the white light L2 and may reflect the excitation light L1. The excitation light L1 having been produced by the mercury vapor lamp 111 passes through teh optical filter 112 and a lens 113 and travels to the change-over mirror 115. The excitation light L1 is then reflected by the change-over mirror 115 and caused by the lens 114 to enter into the light guide 106. The excitation light L1 is guided through the light guide 106 to the leading end of the endoscope 100, and then irradiated through the illuminating lens 102 to the region of interest 10 in the living body, which contains the diseased part 11. The optical filter 112 has the transmission characteristics illustrated in FIG. 9, and the excitation light L1, which has been produced by the mercury vapor lamp 111 and has passed through the optical filter 112, has the line spectrum of a wavelength of 405 nm.

When the region of interest 10 in the living body is exposed to the excitation light L1, it is caused to produce the fluorescence L3. The fluorescence L3 is collected by the objective lens 103, passes through the image fiber 104 and the eyepiece 109, and then travels to the change-over mirror 121. The change-over mirror 121 is driven by the driver 123 in accordance with the signal fed from the timing controller 158 and is moved to the position indicated by the broken line in FIG. 6, that does not obstruct the travel of the fluorescence L3. The fluorescence L3, which has passed over the change-over mirror 121, passes through a lens 141 and the change-over optical filter 142, and the image of the fluorescence L3 is formed on the cold CCD camera 144. The change-over optical filter 142 is provided with the sharp cut filter 142a, which has the light transmission characteristics illustrated in FIG. 8A and transmits the entire fluorescence having wavelengths longer than 460 nm, and the sharp cut filter 142b, which has the light transmission characteristics illustrated in FIG. 8B and transmits only the fluorescence component primarily constituted of the extrinsic fluorescence having wavelengths longer than 630 nm. The sharp cut filters 142a and 142b are changed over to each other by the driver 143, which is operated in accordance with the signal fed from the timing controller 158. The change-over optical filter 142 is thus driven by the driver 143, and the sharp cut filter 142a, which transmits the entire fluorescence having wavelengths of the bluish green color region and longer, is inserted into the optical path of the fluorescence L3. The entire fluorescence passes through the sharp cut filter 142a, and its image is formed on the cold CCD camera 144. The image signal representing the entire fluorescence is fed into the analog-to-digital conversion circuit 151 and digitized by it. The thus obtained digital image signal is stored in the entire fluorescence image memory 153.

Thereafter, the sharp cut filter 142b, which transmits only the fluorescence component primarily constituted of the extrinsic fluorescence, is inserted into the optical path of the fluorescence L3 in accordance with the signal fed from the timing controller 158. As a result, the image signal representing the extrinsic fluorescence is obtained from the cold CCD camera 144. The image signal representing the extrinsic fluorescence is digitized by the analog-to-digital conversion circuit 151, and the thus obtained digital image signal is stored in the extrinsic fluorescence image memory 152.

After the image signals representing the two fluorescence images have thus been obtained, the division memory 155 carries out the division of the output signal, which is fed from the extrinsic fluorescence image memory 152, and the output signal, which is fed from the entire fluorescence image memory 153, by each other. The information representing the results of the division (i.e., a division image signal) is stored in the division memory 155. The division image signal is then fed into the video signal forming circuit 156. In the video signal forming circuit 156, the division image signal is subjected to digital-to-analog conversion and encoding. The division image signal having been obtained from the processing is then fed into the display device 160. The display device 160 reproduces a visible image (a division image) from the division image signal and displays it. When necessary, the visible ordinary image and the visible division image may be overlaid one upon the other on the display surface of the display device 160.

The optical filter 112 located at the mercury vapor lamp 111 may be replaced by an optical filter having different transmission characteristics. For example, as illustrated in FIG. 10, an optical filter capable of selectively transmitting light having a line spectrum of 405 nm and light having a line spectrum of 365 nm may be employed as the optical filter 112. The wavelength of 405 nm is a wavelength $\lambda_{ex1}$ capable of exciting the fluorescent diagnosis drug with a high efficiency, and the wavelength of 365 nm is a wavelength $\lambda_{ex2}$ capable of exciting an intrinsic fluorescence molecule with a high efficiency. Therefore, the combined use of the two kinds of light is desirable for enhancing the signal-to-noise ratio. This also applies to the below-described cases where the fluorescence with the administration of the drug is detected.

The wavelengths $\lambda_{ex1}$ and $\lambda_{ex2}$ are not far apart from each other. Therefore, in the image processing operation, the excitation light intensity $I\lambda_{ex1}$ and the excitation light intensity $I\lambda_{ex2}$ at the region of interest 10 in the living body may be regarded as being of the same distribution of light, and it may be considered that $I\lambda_{ex2}=m \cdot I\lambda_{ex1}$ (where m is an arbitrary fixed number) at the region of interest 10 in the living body. In cases where the excitation light intensity $I\lambda_{ex1}$ and the excitation light intensity $I\lambda_{ex2}$ at the region of interest 10 in the living body are of different distributions of light, it is necessary to provide a matching means.

As described above, in this embodiment, ATX-S10 capable of producing the fluorescence having a wavelength of approximately $\lambda_{em}=670$ nm is employed as the fluorescent diagnosis drug. Therefore, the sharp cut filter 142a, which has the light transmission characteristics illustrated in FIG. 8A and transmits the entire fluorescence having wavelengths longer than 460 nm, and the sharp cut filter 142b, which has the light transmission characteristics illustrated in FIG. 8B and transmits only the fluorescence component primarily constituted of the extrinsic fluorescence having wavelengths longer than 630 nm, are employed. However, the change-over optical filter 142 may be modified when necessary. For example, in cases where 5-ALA capable of producing the fluorescence having a wavelength of approximately $\lambda_{em}=635$ nm is employed as the fluorescent diagnosis drug, a filter having the transmission characteristics such that a cut-off wavelength may be approximately 600 nm may be employed as the sharp cut filter 142b.

Figure 11:
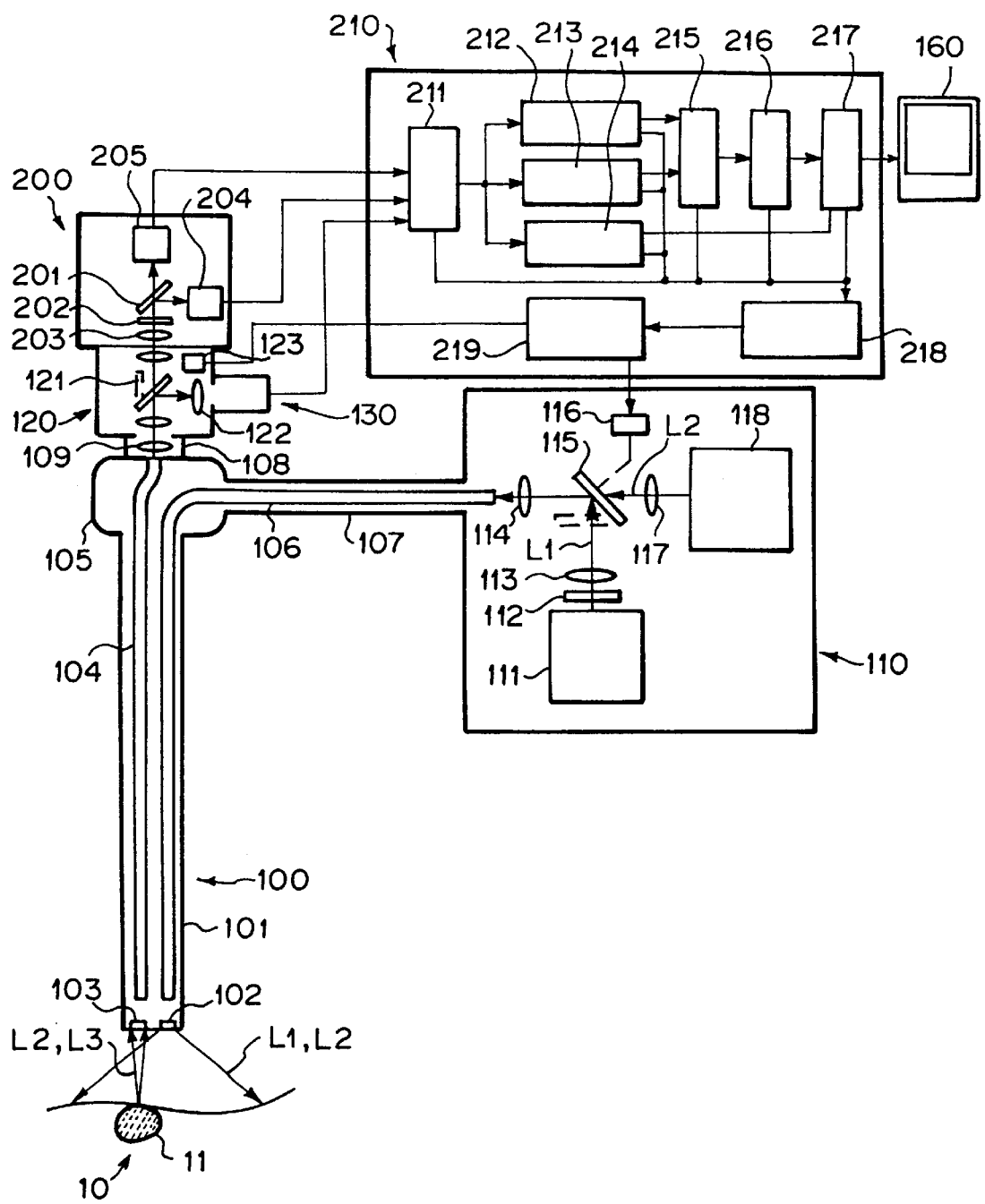
FIG. 11 is a schematic view showing an endoscope system, in which a second embodiment of the fluorescence detecting apparatus in accordance with the present invention is employed.
Figure 12:
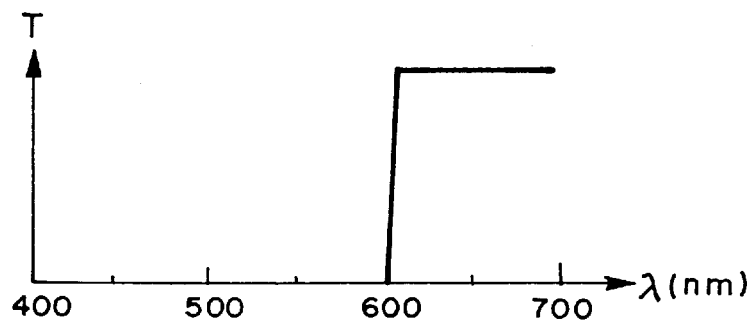
FIG. 12 is a graph showing optical characteristics of a dichroic mirror, which is employed in the second embodiment.

An endoscope system, in which a second embodiment of the fluorescence detecting apparatus in accordance with the present invention is employed, will be described hereinbelow with reference to FIGS. 11 and 12. In FIG. 11, similar elements are numbered with the same reference numerals with respect to FIG. 6. FIG. 11 is a schematic view showing the endoscope system, in which the second embodiment of the fluorescence detecting apparatus in accordance with the present invention is employed. In this endoscope system, excitation light is irradiated to a region of interest in a living body, to which a fluorescent diagnosis drug has been administered, and the fluorescence, which is produced from the region of interest in the living body when the region of interest is exposed to the excitation light, is detected. Also, the extrinsic fluorescence component and a fluorescence sum component, which is the sum of the intrinsic fluorescence component and the extrinsic fluorescence component, are divided by each other.

The endoscope system, in which the second embodiment of the fluorescence detecting apparatus in accordance with the present invention is employed, comprises the endoscope 100 to be inserted into a site of a patient, which site is considered as being a diseased part, and the illuminating device 110 provided with the light sources for producing white light, which is used when an ordinary image is to be obtained, and the excitation light, which is used when a fluorescence image is to be obtained. The endoscope system also comprises the optical path change-over unit 120, which changes the optical path for obtaining the ordinary image, and the optical path for obtaining the fluorescence image, over to each other. The endoscope system further comprises the color CCD camera 130 for detecting the white light, which is reflected from the region of interest 10 in the living body when the ordinary image is to be obtained, and a high-sensitivity camera unit 200 for detecting the fluorescence, which is produced from the region of interest 10 in the living body when the fluorescence image is to be obtained. The endoscope system still further comprises an image processing unit 210 for carrying out image processing on an image signal, which represents the reflected light image or the fluorescence image having been detected, and the display device 160 for reproducing a visible image from the image signal, which has been obtained from the image processing carried out by the image processing unit 210, and displaying the reproduced visible image. This endoscope system is the same as the aforesaid endoscope system, in which the first embodiment of the fluorescence detecting apparatus in accordance with the present invention is employed, except for the constitutions and the effects of the high-sensitivity camera unit 200 and the image processing unit 210.

The high-sensitivity camera unit 200 comprises an excitation light sharp cut filter 202, which filters out the excitation light component, and a dichroic mirror 201. The dichroic mirror 201 separates the fluorescence L3, which has passed through the excitation light sharp cut filter 202, into the extrinsic fluorescence component and the intrinsic fluorescence component. The image of the extrinsic fluorescence is formed on a first cold CCD camera 205, and the image of the intrinsic fluorescence is formed on a second cold CCD camera 204.

The image processing unit 210 comprises an analog-to-digital conversion circuit 211 for digitizing the image signals having been obtained from the CCD cameras. The image processing unit 210 also comprises an ordinary image memory 214 for storing a digitized ordinary image signal. The image processing unit 210 further comprises an extrinsic fluorescence image memory 212 for storing a digitized image signal, which represents the extrinsic fluorescence, and an intrinsic fluorescence image memory 213 for storing a digitized image signal, which represents the intrinsic fluorescence. The image processing unit 210 still further comprises an addition memory 215 for storing the fluorescence sum component, which is the sum of the extrinsic fluorescence component and the intrinsic fluorescence component, and a division memory 216 for carrying out division of the extrinsic fluorescence component and the fluorescence sum component by each other and storing the information representing the results of the division. The image processing unit 210 also comprises a video signal forming circuit 217 for carrying out image processing on the image signal, which is received from the ordinary image memory 214 or the division memory 216, and thereby obtaining a video signal to be used for reproducing the visible image on the display device 160. The image processing unit 210 further comprises a timing controller 219 for feeding signals into the driver 116, which drives the change-over mirror 115 of the illuminating device 110, and the driver 123, which drives the change-over mirror 121 of the optical path change-over unit 120. The image processing unit 210 still further comprises a video processor 218 for controlling the timing controller 219.

When the ordinary image is to be obtained, the endoscope system, in which the second embodiment of the fluorescence detecting apparatus in accordance with the present invention is employed, operates in the same manner as that in the aforesaid endoscope system, in which the first embodiment of the fluorescence detecting apparatus in accordance with the present invention is employed. How the endoscope system operates when the fluorescence image is to be obtained will be described hereinbelow. In this embodiment, 5-ALA capable of producing the fluorescence having a wavelength of approximately $\lambda_{em}$=635 nm is employed as the fluorescent diagnosis drug. The fluorescent diagnosis drug 5-ALA has been administered to the region of interest 10 in the living body.

The change-over mirror 121 is driven by the driver 123 in accordance with the signal fed from the timing controller 219 and is moved to the position indicated by the broken line in FIG. 11, that does not obstruct the travel of the fluorescence L3. The fluorescence L3, which has been produced from the region of interest 10 in the living body when the region of interest 10 is exposed to the excitation light L1, passes over the change-over mirror 121, and passes through the excitation light sharp cut filter 202, which filters out the excitation light component. The fluorescence L3 then travels to the dichroic mirror 201. The dichroic mirror 201 has the transmission characteristics illustrated in FIG. 12, and the image of only the fluorescence component, which is primarily constituted of the extrinsic fluorescence having wavelengths longer than 600 nm, is formed on the first cold CCD camera 205. The fluorescence component, which is primarily constituted of the intrinsic fluorescence having wavelengths shorter than 600 nm, is reflected by the dichroic mirror 201, and the image of this fluorescence component is formed on the second cold CCD camera 204.

The image signal, which is obtained from the first cold CCD camera 205 and represents the extrinsic fluorescence, is fed into the analog-to-digital conversion circuit 211 and digitized by it. The thus obtained digital image signal is stored in the extrinsic fluorescence image memory 212. Also, the image signal, which is obtained from the second cold CCD camera 204 and represents the intrinsic fluorescence, is fed into the analog-to-digital conversion circuit 211 and digitized by it. The thus obtained digital image signal is stored in the intrinsic fluorescence image memory 213. After the image signals representing the two fluorescence images have thus been obtained, the addition memory 215 carries out the addition of the output, which is obtained from the extrinsic fluorescence image memory 212, and the output, which is obtained from the intrinsic fluorescence image memory 213, to each other. The information representing the results of the addition is stored as the addition signal, which represents the fluorescence sum component, in the addition memory 215.

Thereafter, the division memory 216 carries out the division of the output, which is fed from the extrinsic fluorescence image memory 212, and the output, which is fed from the addition memory 215, by each other. The information representing the results of the division (i.e., a division image signal) is stored in the division memory 216. The division image signal is then fed into the video signal forming circuit 217. In the video signal forming circuit 217, the division image signal is subjected to digital-to-analog conversion and encoding. The division image signal having been obtained from the processing is then fed into the display device 160. The display device 160 reproduces a visible image (a division image) from the division image signal and displays it. When necessary, the visible ordinary image and the visible division image may be overlaid one upon the other on the display surface of the display device 160.

Figure 18A:
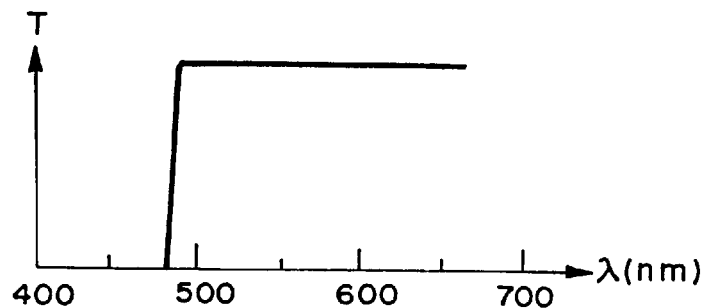
FIGS. 18A, 18B & 18C are graphs showing light transmission characteristics of an optical filter employed in the fifth embodiment.
Figure 18B:
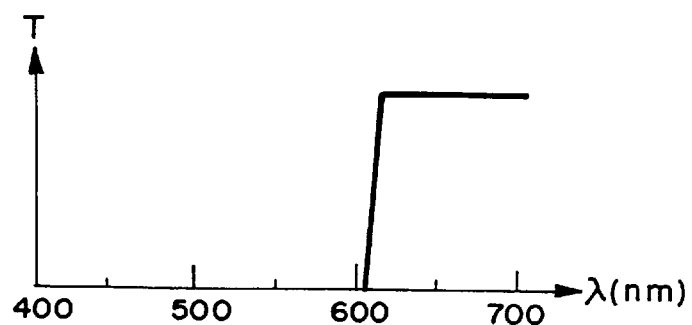
Figure 18C:
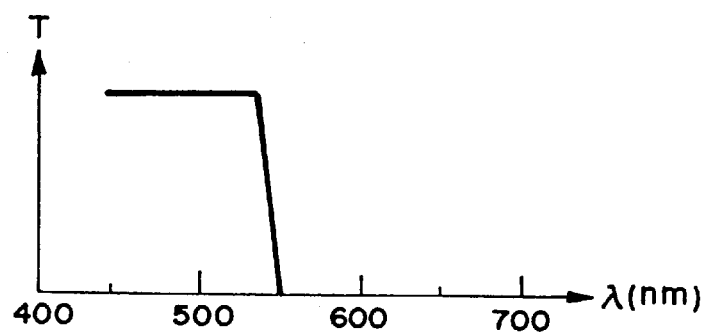

In this embodiment, the separation of the fluorescence L3 with respect to wavelength ranges is carried out by the dichroic mirror 201 alone, and therefore it can be considered that the detection of the fluorescence sum component is substantially equivalent to the detection of the entire fluorescence component. In such cases, an optical filter having the transmission characteristics illustrated in FIG. 18C, such as an optical filter 606, which will be described later, may be located on the front side of the second cold CCD camera 204. In this manner, the fluorescence sum component, which is not equivalent to the entire fluorescence component, may be obtained in the addition memory 215, and the division of the extrinsic fluorescence component and the thus obtained fluorescence sum component by each other may be carried out in the division memory 216.

Figure 14:
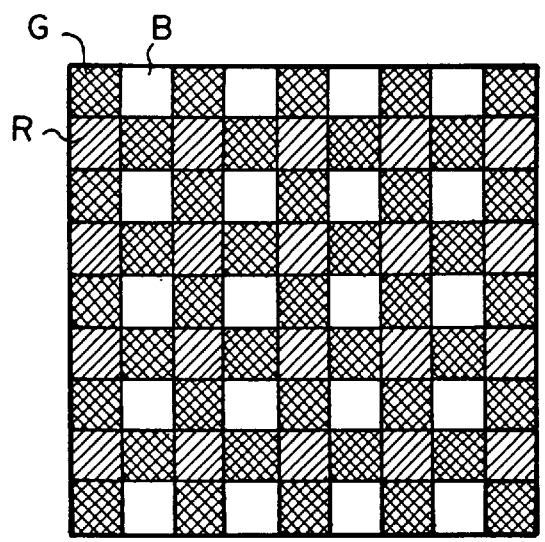
FIG. 14 is an explanatory view showing a mosaic filter, which is used in a high-sensitivity filter employed in the third embodiment.
Figure 13:
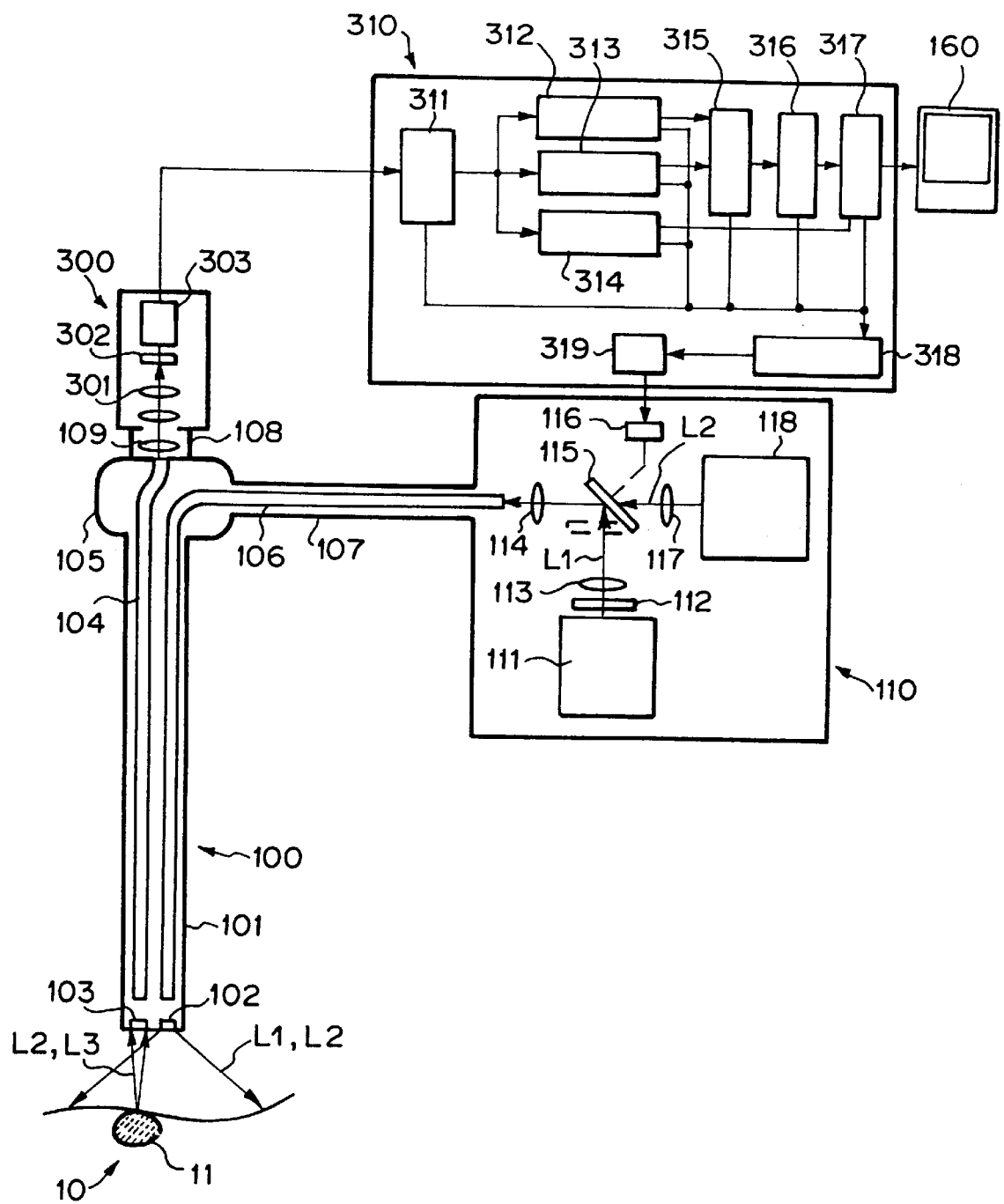
FIG. 13 is a schematic view showing an endoscope system, in which a third embodiment of the fluorescence detecting apparatus in accordance with the present invention is employed.

An endoscope system, in which a third embodiment of the fluorescence detecting apparatus in accordance with the present invention is employed, will be described hereinbelow with reference to FIGS. 13, 14, and 15. In FIG. 13, similar elements are numbered with the same reference numerals with respect to FIG. 6. FIG. 13 is a schematic view showing the endoscope system, in which the third embodiment of the fluorescence detecting apparatus in accordance with the present invention is employed. In this endoscope system, excitation light is irradiated to a region of interest in a living body, to which a fluorescent diagnosis drug has been administered, and the fluorescence, which is produced from the region of interest in the living body when the region of interest is exposed to the excitation light, is detected. Also, a red fluorescence component and a fluorescence sum component, which is the sum of a blue fluorescence component, a green fluorescence component, and the red fluorescence component, are divided by each other.

The endoscope system, in which the third embodiment of the fluorescence detecting apparatus in accordance with the present invention is employed, comprises the endoscope 100 to be inserted into a site of a patient, which site is considered as being a diseased part, and the illuminating device 110 provided with the light sources for producing white light, which is used when an ordinary image is to be obtained, and the excitation light, which is used when a fluorescence image is to be obtained. The endoscope system also comprises a high-sensitivity camera unit 300 for detecting the white light, which is reflected from the region of interest 10 in the living body when the ordinary image is to be obtained, and detecting the fluorescence, which is produced from the region of interest 10 in the living body when the fluorescence image is to be obtained. The endoscope system further comprises an image processing unit 310 for carrying out image processing on an image signal, which represents the reflected light image or the fluorescence image having been detected, and the display device 160 for reproducing a visible image from the image signal, which has been obtained from the image processing carried out by the image processing unit 310, and displaying the reproduced visible image.

This endoscope system is the same as the aforesaid endoscope system, in which the first embodiment of the fluorescence detecting apparatus in accordance with the present invention is employed, except that the optical path change-over unit 120 and the color CCD camera 130 are omitted, and the constitutions and the effects of the high-sensitivity camera unit 300 and the image processing unit 310 are different from those of the high-sensitivity camera unit 200 and the image processing unit 210.

The high-sensitivity camera unit 300 comprises an excitation light sharp cut filter 302, which transmits the reflected white light when the ordinary image is to be obtained, and which filters out the excitation light component of the fluorescence L3 when the fluorescence image is to be obtained. The high-sensitivity camera unit 300 also comprises a cold CCD camera 303, on which the image of the reflected white light having passed through the filter 302 or the image of the fluorescence L3 having passed through the filter 302 is formed. A color mosaic filter, which separates the fluorescence L3 into the components of the R, G, and B wavelength regions, is fitted to the detection surface of the cold CCD camera 303.

The image processing unit 310 comprises an analog-to-digital conversion circuit 311 for digitizing the image signals having been obtained from the CCD cameras. The image processing unit 310 also comprises an R image memory 314 for storing a digitized R image signal, a G image memory 313 for storing a digitized G image signal, and a B image memory 312 for storing a digitized B image signal. The image processing unit 310 further comprises an addition memory 315 for storing an addition signal, which represents the fluorescence sum component obtained by adding the outputs from the image memories to one another, and a division memory 316 for carrying out division of the output from the R image memory 314 and the output from the addition memory 315 by each other and storing the information representing the results of the division. The image processing unit 310 still further comprises a video signal forming circuit 317 for carrying out image processing on the ordinary image signals, which are received from the image memories 312, 313, and 314, or the division image signal, which is received from the division memory 316, and thereby obtaining a video signal to be used for reproducing the visible image on the display device 160. The image processing unit 310 also comprises a timing controller 319 for feeding a signal into the driver 116, which drives the change-over mirror 115 of the illuminating device 110, and a video processor 318 for controlling the timing controller 319.

How the endoscope system, in which the third embodiment of the fluorescence detecting apparatus in accordance with the present invention is employed, operates will be described hereinbelow. Firstly, how the endoscope system operates when the ordinary image is to be obtained will be described hereinbelow.

When the ordinary image is to be obtained, the white light L2, which has been reflected from the region of interest 10 in the living body, is collected by the objective lens 103 and passes through the image fiber 104 and the eyepiece 109, which is located in the eyepiece section 108. The reflected white light L2 then travels to the high-sensitivity camera unit 300. The reflected white light L2, which has passed through the eyepiece 109, passes through a lens 301 and the excitation light sharp cut filter 302, and the image of the reflected white light L2 is formed on the cold CCD camera 303. The color mosaic filter illustrated in FIG. 14 is fitted to the detection surface of the cold CCD camera 303. The color mosaic filter has the optical transmission characteristics illustrated in FIG. 15. The image signal obtained from the cold CCD camera 303 is fed into the analog-to-digital conversion circuit 311. The analog-to-digital conversion circuit 311 digitizes each of R, G, and B image signal components, and the thus obtained digital R, G, and B image signals are stored respectively in the R image memory 314, the G image memory 313, and the B image memory 312. The ordinary image signals, which have thus been stored in the R image memory 314, the G image memory 313, and the B image memory 312, are then fed into the video signal forming circuit 317. In the video signal forming circuit 317, the ordinary image signals are subjected to digital-to-analog conversion, color matrix processing, and encoding. The ordinary image signals having been obtained from the processing are then fed as NTSC signals into the display device 160. The display device 160 reproduces the visible image from the signals and displays it.

How the endoscope system, in which the third embodiment of the fluorescence detecting apparatus in accordance with the present invention is employed, operates when the fluorescence image is to be obtained will be described hereinbelow. In this embodiment, 5-ALA capable of producing the fluorescence having a wavelength of approximately $\lambda_{em}$=635 nm is employed as the fluorescent diagnosis drug. The fluorescent diagnosis drug 5-ALA has been administered to the region of interest 10 in the living body.

The fluorescence L3, which is produced from the region of interest 10 in the living body when the region of interest 10 is exposed to the excitation light L1, is collected by the objective lens 103 and passes through the image fiber 104 and the eyepiece 109. The fluorescence L3 then passes through the excitation light sharp cut filter 302, which filters out the excitation light component. Thereafter, the image of the fluorescence L3 is formed on the cold CCD camera 303. The intensity of the fluorescence L3 is lower than the intensity of the reflected white light L2. Therefore, when the fluorescence image is to be obtained, the imaging rate of the cold CCD camera 303 is set to be sufficiently lower than the imaging rate for obtaining the ordinary image. The fluorescence image signal obtained from the cold CCD camera 303 is fed into the analog-to-digital conversion circuit 311. The analog-to-digital conversion circuit 311 digitizes each of R, G, and B image signal components, and the thus obtained digital R, G, and B image signals are stored respectively in the R image memory 314, the G image memory 313, and the B image memory 312. After the image signals representing the R, G, and B fluorescence images have thus been obtained, the addition memory 315 carries out the addition of the outputs, which are obtained from the R image memory 314, the G image memory 313, and the B image memory 312, to one another. The information representing the results of the addition is stored as the addition signal, which represents the fluorescence sum component, in the addition memory 315. In the fluorescence produced from the living body, the R image signal primarily represents the extrinsic fluorescence, and the B and G image signals primarily represent the intrinsic fluorescence. Therefore, the results of the addition represent the sum of the extrinsic fluorescence and the intrinsic fluorescence.

Thereafter, the division memory 316 carries out the division of the output, which is fed from the R image memory 212, and the output, which is fed from the addition memory 315, by each other. The information representing the results of the division (i.e., a division image signal) is stored in the division memory 316. The division image signal is then fed into the video signal forming circuit 317. In the video signal forming circuit 317, the division image signal is subjected to digital-to-analog conversion and encoding. The division image signal having been obtained from the processing is then fed into the display device 160. The display device 160 reproduces a visible image (a division image) from the division image signal and displays it. When necessary, a memory for storing the ordinary image signal may be employed besides the R, G, and B image memories, and the visible ordinary image and the visible division image and the visible ordinary image may be overlaid one upon the other on the display surface of the display device 160.

In this embodiment, since the intrinsic fluorescence has a high intensity in the G wavelength region, the calculation for obtaining the sum of the intrinsic fluorescence component and the extrinsic fluorescence component may be replaced by the addition of the output from the G image memory 313 and the output from the R image memory 314.

Figure 15:
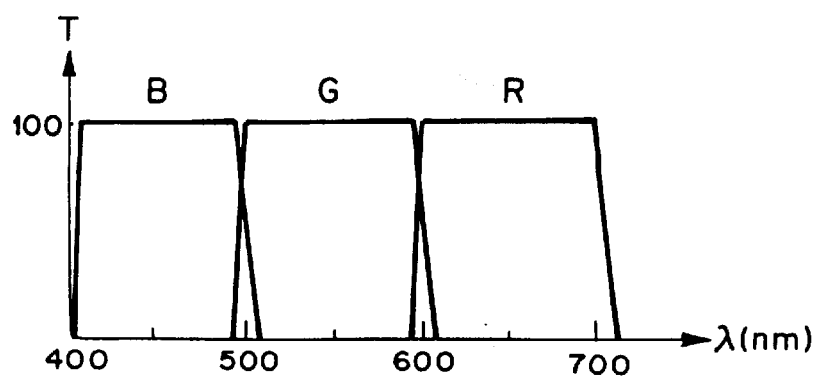
FIG. 15 is a graph showing light transmission characteristics of the mosaic filter shown in FIG. 14.

Also, in this embodiment, the color mosaic filter has the wavelength separation characteristics illustrated in FIG. 15. Therefore, it may be considered that the detection of the fluorescence sum component is substantially equivalent to the detection of the entire fluorescence component. In such cases, the wavelength separation characteristics of the color mosaic filter may be altered (such that, for example, the cut-off characteristics for the respective colors may not overlap one upon another). In this manner, the fluorescence sum component, which is not equivalent to the entire fluorescence component, may be obtained in the addition memory 315, and the division of the R fluorescence component and the thus obtained fluorescence sum component by each other may be carried out in the division memory 316.

In the endoscope system, in which the third embodiment of the fluorescence detecting apparatus in accordance with the present invention is employed, the constitution of the camera unit is simple. Therefore, the endoscope system can be easily constituted as an electronic endoscope, which is provided with an imaging device at the leading end of the endoscope.

Figure 16:
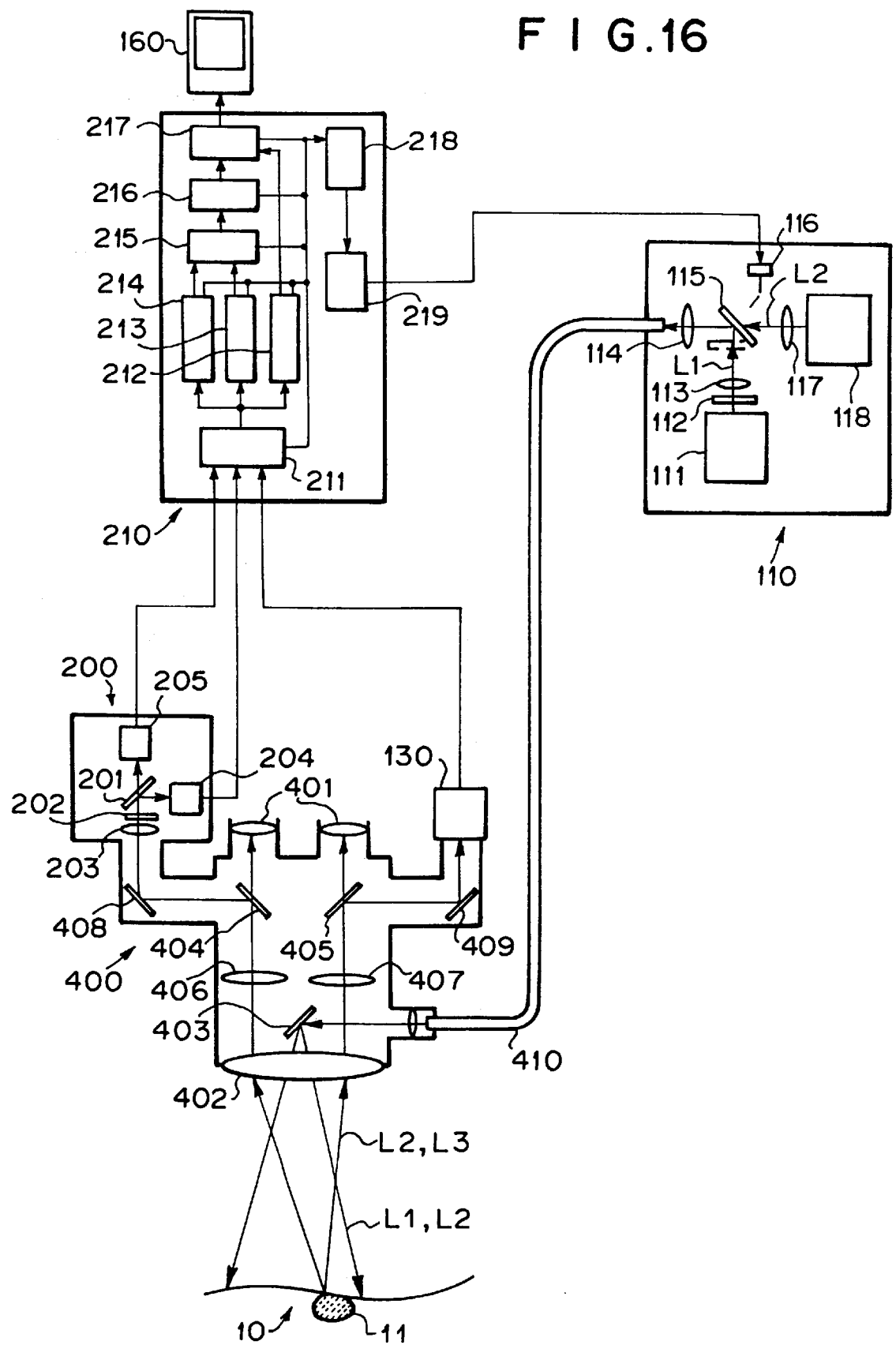
FIG. 16 is a schematic view showing an operating microscope system, in which a fourth embodiment of the fluorescence detecting apparatus in accordance with the present invention is employed.

An operating microscope system, in which a fourth embodiment of the fluorescence detecting apparatus in accordance with the present invention is employed, will be described hereinbelow with reference to FIG. 16. In FIG. 16, similar elements are numbered with the same reference numerals with respect to FIGS. 6 and 11. FIG. 16 is a schematic view showing the operating microscope system, in which the fourth embodiment of the fluorescence detecting apparatus in accordance with the present invention is employed. In this operating microscope system, excitation light is irradiated to a region of interest in a living body, to which a fluorescent diagnosis drug has been administered, and the fluorescence, which is produced from the region of interest in the living body when the region of interest is exposed to the excitation light, is detected. Also, the extrinsic fluorescence component and a fluorescence sum component, which is the sum of the intrinsic fluorescence component and the extrinsic fluorescence component, are divided by each other.

The operating microscope system, in which the fourth embodiment of the fluorescence detecting apparatus in accordance with the present invention is employed, comprises an operating microscope 400 for viewing a site of a patient, which site is considered as being a diseased part, and the illuminating device 110 provided with the light sources for producing white light, which is used when an ordinary image is to be obtained, and the excitation light, which is used when a fluorescence image is to be obtained. The operating microscope system also comprises a light guide 410 for guiding the white light or the excitation light, which has been produced by the illuminating device 110, to the operating microscope 400. The operating microscope system further comprises the color CCD camera 130 for detecting the white light, which is reflected from the region of interest 10 in the living body when the ordinary image is to be obtained, and the high-sensitivity camera unit 200 for detecting the fluorescence, which is produced from the region of interest 10 in the living body when the fluorescence image is to be obtained. The operating microscope system still further comprises the image processing unit 210 for carrying out image processing on an image signal, which represents the reflected light image or the fluorescence image having been detected, and the display device 160 for reproducing a visible image from the image signal, which has been obtained from the image processing carried out by the image processing unit 210, and displaying the reproduced visible image.

The operating microscope 400 comprises a mirror 403 for guiding the white light L2 or the excitation light L1 to the region of interest 10 in the living body. The operating microscope 400 also comprises mirrors 404, 405, 408, and 409 for guiding the reflected white light L2 or the fluorescence L3. The operating microscope 400 further comprises eyepieces 401, 401, and an objective lens 402.

How the operating microscope system, in which the fourth embodiment of the fluorescence detecting apparatus in accordance with the present invention is employed, operates will be described hereinbelow. Firstly, how the operating microscope system operates when the ordinary image is to be obtained will be described hereinbelow.

The reflected white light L2 is collected by the objective lens 402. A portion of the reflected white light L2 passes through the semi-transparent mirrors 404, 405 and the eyepieces 401, 401 and can thus be seen by the operator.

Also, a portion of the reflected white light L2 is reflected by the semi-transparent mirror 405 and the mirror 409, and its image is formed on the color CCD camera 130. The image signal obtained from the color CCD camera 130 is fed into the analog-to-digital conversion circuit 211. The analog-to-digital conversion circuit 211 digitizes each of R, G, and B image signals, and the thus obtained digital R, G, and B image signals are stored in the ordinary image memory 214 corresponding to R,G, and B images. The ordinary image signals are then fed into the video signal forming circuit 217. In the video signal forming circuit 217, the ordinary image signals are subjected to digital-to-analog conversion, color matrix processing, and encoding. The ordinary image signals having been obtained from the processing are then fed as NTSC signals into the display device 160. The display device 160 reproduces the visible image from the signals and displays it.

How the operating microscope system operates when the fluorescence image is to be obtained will be described hereinbelow. In this embodiment, ATX-S10 capable of producing the fluorescence having a wavelength of approximately $\lambda_{em}$=670 nm is employed as the fluorescent diagnosis drug. The fluorescent diagnosis drug ATX-S10 has been administered to the region of interest 10 in the living body.

The excitation light L1, which has been reflected by the change-over mirror 115, is caused by the lens 114 to enter into the light guide 410. The excitation light L1 is guided through the light guide 410 to the operating microscope 400. The excitation light L1 is then reflected by the mirror 403, passes through the objective lens 402, and is thus irradiated to the region of interest 10 in the living body, which contains the diseased part 11. The fluorescence L3, which is produced from the region of interest 10 in the living body, is collected by the objective lens 402 and reflected by the semi-transparent mirror 404 and the mirror 408. The fluorescence L3 then passes through the lens 203 and the excitation light sharp cut filter 202, which filters out the excitation light component. The fluorescence L3 then travels to the dichroic mirror 201. The dichroic mirror 201 has the specific characteristics, and the image of only the fluorescence component, which is primarily constituted of the extrinsic fluorescence having wavelengths longer than 630 nm, is formed on the first cold CCD camera 205. The fluorescence component, which is primarily constituted of the intrinsic fluorescence having wavelengths shorter than 630 nm, is reflected by the dichroic mirror 201, and the image of this fluorescence component is formed on the second cold CCD camera 204.

The image signal, which is obtained from the first cold CCD camera 205 and represents the extrinsic fluorescence, is fed into the analog-to-digital conversion circuit 211 and digitized by it. The thus obtained digital image signal is stored in the extrinsic fluorescence image memory 212. Also, the image signal, which is obtained from the second cold CCD camera 204 and represents the intrinsic fluorescence, is fed into the analog-to-digital conversion circuit 211 and digitized by it. The thus obtained digital image signal is stored in the intrinsic fluorescence image memory 213.

After the image signals representing the two fluorescence images have thus been obtained, the addition memory 215 carries out the addition of the output, which is obtained from the extrinsic fluorescence image memory 212, and the output, which is obtained from the intrinsic fluorescence image memory 213, to each other. The information representing the results of the addition is stored in the addition memory 215.

Thereafter, the division memory 216 carries out the division of the output, which is fed from the extrinsic fluorescence image memory 212, and the output, which is fed from the addition memory 215, by each other. The information representing the results of the division (i.e., a division image signal) is stored in the division memory 216. The division image signal is then fed into the video signal forming circuit 217. In the video signal forming circuit 217, the division image signal is subjected to digital-to-analog conversion and encoding. The division image signal having been obtained from the processing is then fed into the display device 160. The display device 160 reproduces a visible image (a division image) from the division image signal and displays it. When necessary, the visible ordinary image and the visible division image may be overlaid one upon the other on the display surface of the display device 160.

In this embodiment, as in the endoscope system utilizing the second embodiment shown in FIG. 11, the separation of the fluorescence L3 with respect to wavelength ranges is carried out by the dichroic mirror 201 alone, and therefore it can be considered that the detection of the fluorescence sum component is substantially equivalent to the detection of the entire fluorescence component. In such cases, an optical filter having the transmission characteristics illustrated in FIG. 18C, such as the optical filter 606, which will be described later, may be located on the front side of the second cold CCD camera 204. In this manner, the fluorescence sum component, which is not equivalent to the entire fluorescence component, may be obtained in the addition memory 215, and the division of the extrinsic fluorescence component and the thus obtained fluorescence sum component by each other may be carried out in the division memory 216.

The sharp cut filters used in the systems, in which the first, second, third, and fourth embodiments are employed, may be modified in accordance with the wavelength range of the excitation light.

In the first, second, third, and fourth embodiments described above, the fluorescence with the administration of the drug is detected. The first, second, third, and fourth embodiments described above are also applicable to autofluorescence diagnosing systems, in which the autofluorescence without the administration of the drum is detected. In such cases, each of the constitutions of the first, second, third, and fourth embodiments may be applied approximately directly. In such cases, light having wavelengths, which fall within a wavelength range in the vicinity of the excitation peak wavelength for the intrinsic dye in the living body, may be employed as the excitation light.

Figure 17:
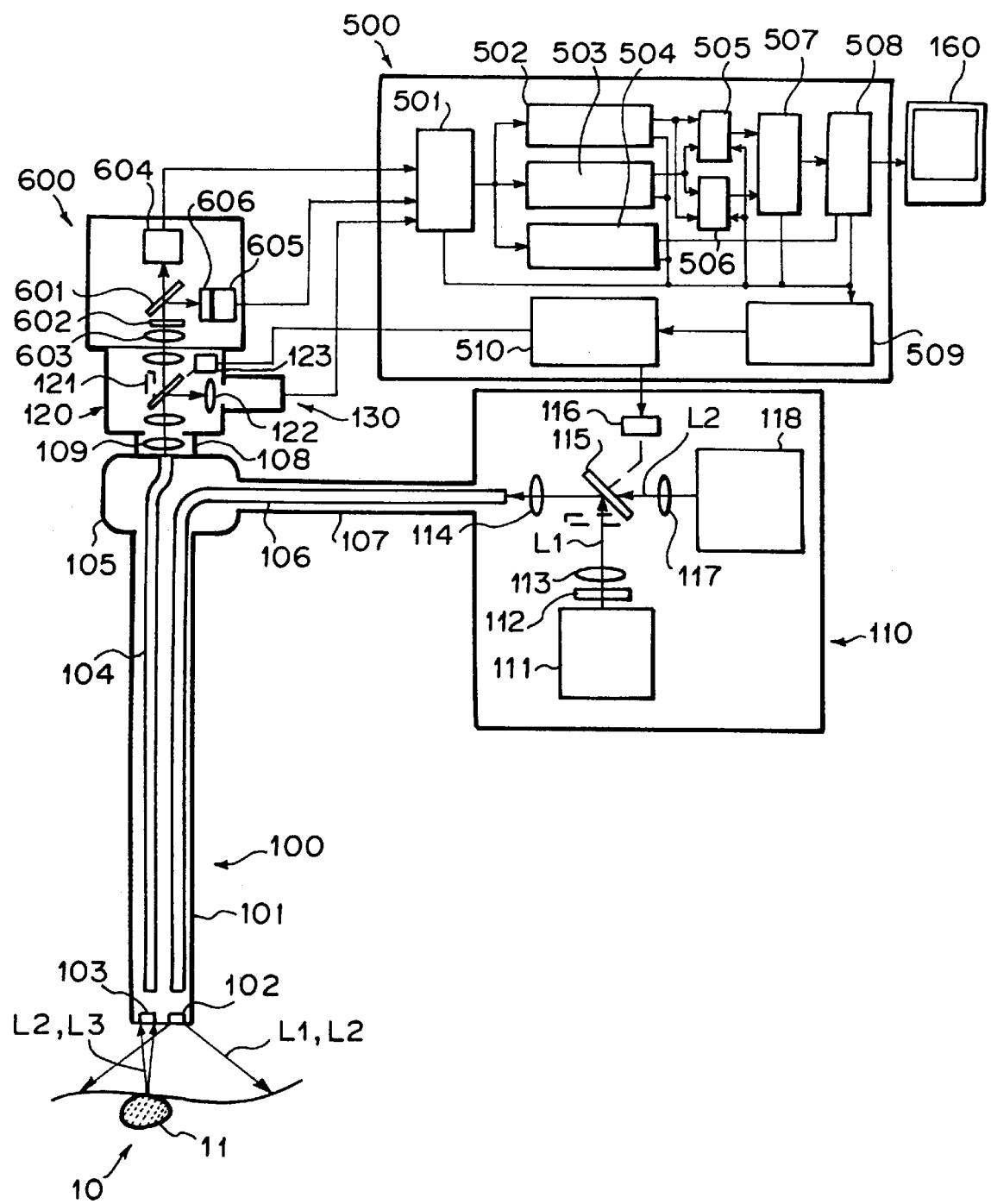
FIG. 17 is a schematic view showing an endoscope system, in which a fifth embodiment of the fluorescence detecting apparatus in accordance with the present invention is employed.

In the embodiments described above, the division of the extrinsic fluorescence component or the long wavelength component (for example, the red fluorescence component R) is carried out. The fluorescence detecting apparatus in accordance with the present invention is also applicable when the division of a fluorescence difference component, (In−Ex) or (G−R), is carried out. Such an embodiment will be described hereinbelow with reference to FIGS. 17 and 18. In FIG. 17, similar elements are numbered with the same reference numerals with respect to FIG. 6. FIG. 17 is a schematic view showing an endoscope system, in which a fifth embodiment of the fluorescence detecting apparatus in accordance with the present invention is employed. In this endoscope system, excitation light is irradiated to a region of interest in a living body, to which no fluorescent diagnosis drug has been administered, and the intrinsic fluorescence, which is produced from the region of interest in the living body when the region of interest is exposed to the excitation light, is detected. Also, the fluorescence difference component (G−R) and a fluorescence sum component (G+R) are divided by each other.

The endoscope system, in which the fifth embodiment of the fluorescence detecting apparatus in accordance with the present invention is employed, comprises the endoscope 100 to be inserted into a site of a patient, which site is considered as being a diseased part, and the illuminating device 110 provided with the light sources for producing white light, which is used when an ordinary image is to be obtained, and the excitation light, which is used when a fluorescence image is to be obtained. The endoscope system also comprises the optical path change-over unit 120, which changes the optical path for obtaining the ordinary image, and the optical path for obtaining the fluorescence image, over to each other. The endoscope system further comprises the color CCD camera 130 for detecting the white light, which is reflected from the region of interest 10 in the living body when the ordinary image is to be obtained, and a high-sensitivity camera unit 600 for detecting the fluorescence, which is produced from the region of interest 10 in the living body when the fluorescence image is to be obtained. The endoscope system still further comprises an image processing unit 500 for carrying out image processing on an image signal, which represents the reflected light image or the fluorescence image having been detected, and the display device 160 for reproducing a visible image from the image signal, which has been obtained from the image processing carried out by the image processing unit 500, and displaying the reproduced visible image. This endoscope system is the same as the aforesaid endoscope system, in which the first embodiment of the fluorescence detecting apparatus in accordance with the present invention is employed, except for the constitutions and the effects of the high-sensitivity camera unit 600 and the image processing unit 500.

The high-sensitivity camera unit 600 comprises an optical filter 602, which filters out the excitation light component, and a dichroic mirror 601. The dichroic mirror 601 separates the fluorescence L3, which has passed through the optical filter 602, into the fluorescence component, which has wavelengths falling within the red wavelength range, and the fluorescence component, which has wavelengths shorter than the red wavelength range. The dichroic mirror 601 transmits the fluorescence component, which has wavelengths falling within the red wavelength range, and forms its image on a first high-sensitivity camera 604. Also, the dichroic mirror 601 reflects the fluorescence component, which has wavelengths shorter than the red wavelength range, toward a second high-sensitivity camera 605. An optical filter 606, which transmits only the fluorescence component having wavelengths falling within the green wavelength range and filters out the other fluorescence component contained in the fluorescence component having wavelengths shorter than the red wavelength range, is located in front of the second high-sensitivity camera 605.

The image processing unit 500 comprises an analog-to-digital conversion circuit 501 for digitizing the image signals having been obtained from the high-sensitivity cameras. The image processing unit 500 also comprises an ordinary image memory 502 for storing a digitized ordinary image signal. The image processing unit 500 further comprises a red fluorescence image memory 503 for storing a digitized image signal, which represents the red fluorescence component, and a green fluorescence image memory 504 for storing a digitized image signal, which represents the green fluorescence component. The image processing unit 500 still further comprises a subtraction memory 505 for storing the fluorescence difference component, which is obtained by subtracting the red fluorescence component and the green fluorescence component from each other. The image processing unit 500 also comprises an addition memory 506 for storing the fluorescence sum component, which is the sum of the green fluorescence component and the red fluorescence component, and a division memory 507 for carrying out division of the fluorescence difference component and the fluorescence sum component by each other and storing the information representing the results of the division. The image processing unit 500 further comprises a video signal forming circuit 508 for carrying out image processing on the image signal, which is received from the ordinary image memory 502 or the division memory 507, and thereby obtaining a video signal to be used for reproducing the visible image on the display device 160. The image processing unit 500 still further comprises a timing controller 510 for feeding signals into the driver 116, which drives the change-over mirror 115 of the illuminating device 110, and the driver 123, which drives the change-over mirror 121 of the optical path change-over unit 120. The image processing unit 500 also further comprises a video processor 509 for controlling the timing controller 510.

When the ordinary image is to be obtained, the endoscope system, in which the fifth embodiment of the fluorescence detecting apparatus in accordance with the present invention is employed, operates in the same manner as that in the aforesaid endoscope system, in which the first embodiment of the fluorescence detecting apparatus in accordance with the present invention is employed. How the endoscope system operates when the fluorescence image is to be obtained will be described hereinbelow.

The change-over mirror 121 is driven by the driver 123 in accordance with the signal fed from the timing controller 510 and is moved to the position indicated by the broken line in FIG. 17, that does not obstruct the travel of the fluorescence L3. The fluorescence L3, which has been produced from the region of interest 10 in the living body when the region of interest 10 is exposed to the excitation light L1, passes over the change-over mirror 121, and passes through the optical filter 602. The fluorescence L3 then travels to the dichroic mirror 601. The optical filter 602 has the transmission characteristics illustrated in FIG. 18A and transmits only the fluorescence having wavelengths longer than 480 nm. By the optical filter 602, the excitation light L1 having a middle wavelength of 405 nm is filtered out. The dichroic mirror 601 has the transmission characteristics illustrated in FIG. 18B and transmits only the red fluorescence component having wavelengths longer than 610 nm. Therefore, only the red fluorescence component impinges upon the first high-sensitivity camera 604. Also, the dichroic mirror 601 reflects the fluorescence component, which has wavelengths shorter than 610 nm, toward the second high-sensitivity camera 605. The optical filter 606, which is located in front of the second high-sensitivity camera 605, has the transmission characteristics illustrated in FIG. 18C. The optical filter 606 transmits only the fluorescence component, which has wavelengths shorter than 540 nm, and filters out the other fluorescence component contained in the fluorescence component, which has wavelengths shorter than 610 nm and has been reflected from the dichroic mirror 601. Therefore, only the green fluorescence component, which has wavelengths of between 480 nm and 540 nm, impinges upon the second high-sensitivity camera 605.

The image signal, which is obtained from the first high-sensitivity camera 604 and represents the red fluorescence, is fed into the analog-to-digital conversion circuit 501 and digitized by it. The thus obtained digital image signal is stored in the red fluorescence image memory 503. Also, the image signal, which is obtained from the second high-sensitivity camera 605 and represents the green fluorescence, is fed into the analog-to-digital conversion circuit 501 and digitized by it. The thus obtained digital image signal is stored in the green fluorescence image memory 504.

Thereafter, the subtraction memory 505 subtracts the output, which is obtained from the red fluorescence image memory 503, and the output, which is obtained from the green fluorescence image memory 504, from each other and stores the thus obtained difference image signal. Also, the addition memory 506 carries out the addition of the output, which is obtained from the red fluorescence image memory 503, and the output, which is obtained from the green fluorescence image memory 504, to each other and stores the thus obtained addition image signal. Further, the division memory 507 carries out the division of the output, which is fed from the subtraction memory 505, and the output, which is fed from the addition memory 506, by each other and stores the thus obtained division image signal. The division image signal is then fed into the video signal forming circuit 508. In the video signal forming circuit 508, the division image signal is subjected to digital-to-analog conversion and encoding. The division image signal having been obtained from the processing is then fed into the display device 160. The display device 160 reproduces a visible image (a division image) from the division image signal and displays it. When necessary, the visible ordinary image and the visible division image may be overlaid one upon the other on the display surface of the display device 160.

In the fifth embodiment, the division of the fluorescence difference component (G−R) and the fluorescence sum component (G+R) by each other is carried out. Alternatively, the transmission characteristics of the optical filters 602 and 606 and the dichroic mirror 601 may be altered (for example, the cut-off wavelengths of the optical filter 606 and the dichroic mirror 601 may be set to be identical with each other). In this manner, the division of the fluorescence difference component (G−R) and the entire fluorescence component by each other may be carried out.

Also, in the fifth embodiment, the autofluorescence without the administration of the drum is detected. This embodiment is also applicable when the fluorescence with the administration of the drug is detected. In such cases, the constitution of this embodiment may be applied approximately directly. In such cases, light having wavelengths, which fall within a wavelength range in the vicinity of the excitation peak wavelength for the fluorescent diagnosis drug (when necessary, also for the intrinsic dye in the living body), may be employed as the excitation light.

In the embodiments described above, the fluorescence detecting apparatus in accordance with the present invention is employed in the imaging optical system. However, the fluorescence detecting apparatus in accordance with the present invention is also applicable to scanning optical systems. In such cases, the fluctuation ηD in the detection efficiency due to the distance between the fluorescence producing site and the fluorescence receiving optical system, or the like, can be canceled.

What is claimed is:

1. A fluorescence detecting apparatus, comprising:
   i) an excitation light irradiating means for irradiating excitation light to a region of interest in a living body, said excitation light having wavelengths falling within an excitation wavelength range for an intrinsic dye in the living body, which intrinsic dye is capable of producing fluorescence when it is excited with said excitation light,
   ii) a first fluorescence detecting means for detecting a first fluorescence component, which is either one of:
      a) an entire intrinsic fluorescence component having wavelengths falling within a visible wavelength range, which contains a comparatively short wavelength range and a comparatively long wavelength range among the wavelength range of intrinsic fluorescence, that is produced by said intrinsic dye in said region of interest in the living body, and
      b) a fluorescence sum component, which is the sum of a fluorescence component having wavelengths falling within a part of the comparatively short wavelength range among the wavelength range of the intrinsic fluorescence, that is produced by said intrinsic dye in said region of interest in the living body, and a fluorescence component having wavelengths falling within a part of the comparatively long wavelength range among the wavelength range of the intrinsic fluorescence,
   iii) a second fluorescence detecting means for detecting a second fluorescence component, which is either one of:
      a) a fluorescence component having wavelengths falling within a part of the comparatively long wavelength range among the wavelength range of the intrinsic fluorescence, and
      b) a fluorescence difference component, which is the difference between a fluorescence component, that have wavelengths falling within a part of the comparatively short wavelength range among the wavelength range of the intrinsic fluorescence, and a fluorescence component, that has wavelengths falling within a part of the comparatively long wavelength range among the wavelength range of the intrinsic fluorescence, and
   iv) a division means for carrying out a division of said first fluorescence component, which has been detected by said first fluorescence detecting means, by said second fluorescence component, which has been detected by said second fluorescence detecting means.

2. An apparatus as defined in claim 1 wherein light having wavelengths falling within a wavelength range in the vicinity of an excitation peak wavelength for said intrinsic dye in the living body is employed as said excitation light.

3. An apparatus as defined in claim 1 wherein each of said first fluorescence detecting means and said second fluorescence detecting means carries out two-dimensional detection of the fluorescence, which is produced from said region of interest so as to obtain a fluorescence image of said region of interest.

4. A fluorescence detecting apparatus, comprising:
   i) an excitation light irradiating projector for irradiating excitation light to a region of interest in a living body, said excitation light having wavelengths falling within an excitation wavelength range for an intrinsic dye in the living body, which intrinsic dye is capable of producing fluorescence when it is excited with said excitation light,
   ii) a first fluorescence detector for detecting a first fluorescence component, which is either one of:
      a) an entire intrinsic fluorescence component having wavelengths falling within a visible wavelength range, which contains a comparatively short wavelength range and a comparatively long wavelength range among the wavelength range of intrinsic fluorescence, that is produced by said intrinsic dye in said region of interest in the living body, and b) a fluorescence sum component, which is the sum of a fluorescence component having wavelengths falling within a part of the comparatively short wavelength range among the wavelength range of the intrinsic fluorescence, that is produced by said intrinsic dye in said region of interest in the living body, and a fluorescence component having wavelengths falling within a part of the comparatively long wavelength range among the wavelength range of the intrinsic fluorescence, iii) a second fluorescence detector for detecting a second fluorescence component, which is either one of:

a) a fluorescence component having wavelengths falling within a part of the comparatively long wavelength range among the wavelength range of the intrinsic fluorescence, and b) a fluorescence difference component, which is the difference between a fluorescence component, that have wavelengths falling within a part of the comparatively short wavelength range among the wavelength range of the intrinsic fluorescence, and a fluorescence component, that has wavelengths falling within a part of the comparatively long wavelength range among the wavelength range of the intrinsic fluorescence, and iv) a divider for dividing said first fluorescence component, which has been detected by said first fluorescence detector, by said second fluorescence component, which has been detected by said second fluorescence detector.

5. An apparatus as defined in claim 4 wherein light having wavelengths falling within a wavelength range in the vicinity of an excitation peak wavelength for said intrinsic dye in the living body is employed as said excitation light.

6. An apparatus as defined in claim 4 wherein each of said first fluorescence detecting means and said second fluorescence detecting means carries out two-dimensional detection of the fluorescence, which is produced from said region of interest so as to obtain a fluorescence image of said region of interest.

* * * * *